US010975040B2

(12) United States Patent
Mahadevan et al.

(10) Patent No.: US 10,975,040 B2
(45) Date of Patent: *Apr. 13, 2021

(54) HYDROXYPHENYL NAPHTHOTRIAZOLES AS POLYMERIZABLE BLOCKERS OF HIGH ENERGY LIGHT

(71) Applicant: Johnson & Johnson Vision Care, Inc., Jacksonville, FL (US)

(72) Inventors: Shivkumar Mahadevan, Jacksonville, FL (US); Leilani K. Sonoda, Atlantic Beach, FL (US); Dola Sinha, Jacksonville, FL (US); Patricia Martin, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,001

(22) Filed: Nov. 15, 2019

(65) Prior Publication Data
US 2020/0079743 A1 Mar. 12, 2020

Related U.S. Application Data

(63) Continuation of application No. 15/979,619, filed on May 15, 2018, now Pat. No. 10,526,296.

(60) Provisional application No. 62/527,106, filed on Jun. 30, 2017.

(51) Int. Cl.
| | | |
|---|---|---|
| *G02B 1/04* | (2006.01) | |
| *C07D 249/22* | (2006.01) | |
| *C08G 77/20* | (2006.01) | |
| *C08J 3/075* | (2006.01) | |
| *C08G 77/442* | (2006.01) | |

(52) U.S. Cl.
CPC ........... *C07D 249/22* (2013.01); *C08G 77/20* (2013.01); *C08G 77/442* (2013.01); *C08J 3/075* (2013.01); *C08J 2383/04* (2013.01); *G02B 1/04* (2013.01); *G02B 1/043* (2013.01)

(58) Field of Classification Search
CPC .............................. G02B 1/043; C07D 249/22
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 3,769,294 A | 10/1973 | Catino et al. |
| 3,808,178 A | 4/1974 | Gaylord |
| 4,113,224 A | 9/1978 | Clark et al. |
| 4,120,570 A | 10/1978 | Gaylord |
| 4,136,250 A | 1/1979 | Mueller et al. |
| 4,153,641 A | 5/1979 | Deichert et al. |
| 4,197,266 A | 4/1980 | Clark et al. |
| 4,436,887 A | 3/1984 | Chromecek et al. |
| 4,495,313 A | 1/1985 | Larsen |
| 4,659,782 A | 4/1987 | Spinelli |
| 4,659,783 A | 4/1987 | Spinelli |
| 4,740,533 A | 4/1988 | Su et al. |
| 4,889,664 A | 12/1989 | Kindt-Larsen et al. |
| 4,910,277 A | 3/1990 | Bambury et al. |
| 5,006,622 A | 4/1991 | Kunzler et al. |
| 5,034,461 A | 7/1991 | Lai et al. |
| 5,039,459 A | 8/1991 | Kindt-Larsen et al. |
| 5,070,215 A | 12/1991 | Bambury et al. |
| 5,236,969 A | 8/1993 | Kunzler et al. |
| 5,244,981 A | 9/1993 | Seidner et al. |
| 5,270,418 A | 12/1993 | Kunzler et al. |
| 5,298,533 A | 3/1994 | Nandu et al. |
| 5,314,960 A | 5/1994 | Spinelli et al. |
| 5,331,067 A | 7/1994 | Seidner et al. |
| 5,371,147 A | 12/1994 | Spinelli et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,824,719 A | 10/1998 | Kunzler et al. |
| 5,849,811 A | 12/1998 | Nicolson et al. |
| 5,945,465 A | 8/1999 | Ozark et al. |
| 5,962,548 A | 10/1999 | Vanderlaan et al. |
| 5,965,631 A | 10/1999 | Nicolson et al. |
| 5,977,219 A | 11/1999 | Ravichandran et al. |
| 5,998,498 A | 12/1999 | Vanderlaan et al. |
| 6,020,445 A | 2/2000 | Vanderlaan et al. |
| 6,087,415 A | 7/2000 | Vanderlaan et al. |
| 6,166,218 A | 12/2000 | Ravichandran et al. |

(Continued)

FOREIGN PATENT DOCUMENTS

| | | |
|---|---|---|
| EP | 0080539 B1 | 6/1983 |
| EP | 0131468 B1 | 1/1985 |

(Continued)

OTHER PUBLICATIONS

PCT International Preliminary Report on Patentability, dated Dec. 31, 2019, for PCT Int'l Appln. No. PCT/IB2018/053669.
PCT International Preliminary Report on Patentability, dated Dec. 31, 2019, for PCT Int'l Appln. No. PCT/IB2018/054588.
Belusa, J. et al, 2- (2-Hydroxyphenyl)benzotriazoles. I. Synthesis arid their ultraviolet and infrared spectra, Chem.zvesti 1974, vol. 28, No. 5, pp. 673-679.
Berthon, et al., Synthesis, Electrochemical and Spectroscopic Properties of Pendant Hydroquinone-and Quinone-Substitued Polypyridyl Ruthenium (11) Complex, Inorganica Chimica Acta, 1993, pp. 3-7, vol. 204.
Compendium of Polymer Terminology arid Nomenclature: IUPAC Recommendations 2008, edited by: Richard G. Jones, Jaroslav Kahovec, Robert Stepto, Edward S. Wilks, Michael Hess, Tatsuki Kitayarna, and W. Val Metanomski.

(Continued)

*Primary Examiner* — Michael F Pepitone
(74) *Attorney, Agent, or Firm* — Raef M. Shaltout

(57) ABSTRACT

Described are high energy light blocking compounds and ophthalmic devices containing the compounds. In particular, described are hydroxyphenyl naphthotriazole structures with polymerizable functionality that block high energy light and are visibly transparent. The hydroxyphenyl naphthotriazole structures can be incorporated into ophthalmic devices, such as hydrogel contact lenses, to protect eyes from high energy light radiation.

20 Claims, 3 Drawing Sheets

(56) References Cited

U.S. PATENT DOCUMENTS

| | | |
|---|---|---|
| 6,244,707 B1 | 6/2001 | Faubi |
| 6,367,929 B1 | 4/2002 | Maiden et al. |
| 6,420,453 B1 | 7/2002 | Bowers et al. |
| 6,423,761 B1 | 7/2002 | Bowers et al. |
| 6,767,979 B1 | 7/2004 | Muir et al. |
| 6,822,016 B2 | 11/2004 | McCabe et al. |
| 6,867,245 B2 | 3/2005 | Iwata et al. |
| 6,943,203 B2 | 9/2005 | Vanderlaan et al. |
| 6,951,894 B1 | 10/2005 | Nicolson et al. |
| 7,052,131 B2 | 5/2006 | McCabe et al. |
| 7,247,692 B2 | 7/2007 | Laredo |
| 7,249,848 B2 | 7/2007 | Laredo et al. |
| 7,396,890 B2 | 7/2008 | Zanini et al. |
| 7,461,937 B2 | 12/2008 | Steffen et al. |
| 7,468,398 B2 | 12/2008 | Nicolson et al. |
| 7,538,146 B2 | 5/2009 | Nicolson et al. |
| 7,553,880 B2 | 6/2009 | Nicolson et al. |
| 7,572,841 B2 | 8/2009 | Chen et al. |
| 7,666,921 B2 | 2/2010 | McCabe et al. |
| 7,691,916 B2 | 4/2010 | McCabe et al. |
| 7,786,185 B2 | 8/2010 | Rathore et al. |
| 7,803,359 B1 | 9/2010 | Jinkerson et al. |
| 7,825,170 B2 | 11/2010 | Steffen et al. |
| 7,915,323 B2 | 3/2011 | Awasthi et al. |
| 7,934,830 B2 | 5/2011 | Blackwell et al. |
| 7,956,131 B2 | 6/2011 | Arnold et al. |
| 7,994,356 B2 | 6/2011 | Awasthi et al. |
| 8,022,158 B2 | 9/2011 | Rathore et al. |
| 8,026,326 B2 | 9/2011 | Benz et al. |
| 8,043,607 B2 | 10/2011 | Jinkerson |
| 8,138,290 B2 | 3/2012 | Blackwell et al. |
| 8,163,206 B2 | 4/2012 | Chang et al. |
| 8,236,053 B1 | 8/2012 | Freeman |
| 8,273,802 B2 | 9/2012 | Laredo et al. |
| 8,323,631 B2 | 12/2012 | Jinkerson |
| 8,360,574 B2 | 1/2013 | Ishak et al. |
| 8,389,597 B2 | 3/2013 | Blackwell et al. |
| 8,399,538 B2 | 3/2013 | Steffen et al. |
| 8,415,404 B2 | 4/2013 | Nicolson et al. |
| 8,420,711 B2 | 4/2013 | Awasthi et al. |
| 8,450,387 B2 | 5/2013 | McCabe et al. |
| 8,470,906 B2 | 6/2013 | Rathore et al. |
| 8,476,390 B2 | 7/2013 | Benz et al. |
| 8,487,058 B2 | 7/2013 | Liu et al. |
| 8,507,577 B2 | 8/2013 | Zanini et al. |
| 8,568,626 B2 | 10/2013 | Nicolson et al. |
| 8,618,323 B2 | 12/2013 | Benz et al. |
| 8,637,621 B2 | 1/2014 | Iwata et al. |
| 8,703,891 B2 | 4/2014 | Broad |
| 8,807,745 B2 | 8/2014 | Nunez et al. |
| 8,940,812 B2 | 1/2015 | Reboul et al. |
| 8,980,972 B2 | 3/2015 | Driver |
| 9,056,878 B2 | 6/2015 | Fujisawa et al. |
| 9,057,821 B2 | 6/2015 | Broad et al. |
| 9,125,829 B2 | 9/2015 | Bonda et al. |
| 9,170,349 B2 | 10/2015 | Mahadevan et al. |
| 9,217,813 B2 | 12/2015 | Liu et al. |
| 9,244,196 B2 | 1/2016 | Scales et al. |
| 9,260,544 B2 | 2/2016 | Rathore et al. |
| 9,297,928 B2 | 3/2016 | Molock et al. |
| 9,297,929 B2 | 3/2016 | Scales et al. |
| 9,765,051 B2 | 9/2017 | Bonda et al. |
| 9,927,635 B2 | 3/2018 | Ishak et al. |
| 10,526,296 B2 * | 1/2020 | Mahadevan ......... C08G 77/442 |
| 2010/0048847 A1 | 2/2010 | Broad |
| 2010/0168359 A1 | 7/2010 | Domschke et al. |
| 2013/0168617 A1 | 7/2013 | Alli et al. |
| 2013/0172440 A1 | 7/2013 | Alli et al. |
| 2013/0217620 A1 | 8/2013 | Alli et al. |
| 2014/0024791 A1 | 1/2014 | Alli et al. |
| 2014/0031447 A1 | 1/2014 | Alli et al. |
| 2014/0044654 A1 | 2/2014 | Bonda et al. |
| 2015/0094395 A1 | 4/2015 | Alli et al. |
| 2015/0164652 A1 | 6/2015 | Bonda et al. |
| 2015/0175732 A1 | 6/2015 | Awasthi et al. |
| 2016/0002200 A1 | 1/2016 | Bonda et al. |
| 2016/0022555 A1 | 1/2016 | Bonda et al. |

FOREIGN PATENT DOCUMENTS

| | | |
|---|---|---|
| EP | 0924203 A1 | 6/1999 |
| EP | 2123638 A1 | 11/2009 |
| GB | 217810 | 6/1924 |
| GB | 2319035 A | 5/1998 |
| JP | 2004277581 | 10/2004 |
| JP | 4627009 B2 | 2/2011 |
| WO | 1999063366 A1 | 12/1999 |
| WO | 2001030866 A1 | 5/2001 |
| WO | 200212205 A1 | 2/2002 |
| WO | 200242281 A1 | 5/2002 |
| WO | 2003/022321 A2 | 3/2003 |
| WO | 2003089519 A1 | 10/2003 |
| WO | 2007050395 A2 | 5/2007 |
| WO | 2008061992 A2 | 5/2008 |
| WO | 2013055746 A1 | 4/2013 |
| WO | 2014025370 A1 | 2/2014 |
| WO | 2017/073467 A1 | 5/2017 |

OTHER PUBLICATIONS

Crivello, et al, Photoinitiators for Free Radical Cationic & Anionic Photopolymerisation, 2nd Edition, vol. III, pp. 275-298, John Wley and Sons, New York, 1998.

Doutch et al, Ultraviolet Light Transmission through the Human Corneal Stroma Is Reduced in the Periphery, Biophysical Journal, vol. 102, Mar. 2012, pp. 1258-1264.

Hafez et al, Carbonyl and Thiocarbonyl Compounds. V. Synthesis of Newer Unsaturated Nitriles, Carboxylic Acids, and Esters Derived from Xanthene and Thiaxanthene, Journal of Organic Chemistry, vol. 26, pp. 3988-3991, Oct. 1961.

Ham et al., "Retinal sensitivity to damage from short wavelength light." Nature 260 (1976), pp. 153-155.

Jockusch et al, Photostabilization of Endogenous Porphyrins: Excited State Quenching by Fused Ring Cyanoacrylates, Photchemical & Photobiological Sciences, 2014, vol. 13, No. 8, pp. 1180-1184.

Larn, et al., Synthesis of Dinucleating Phenanthroline-Based Ligands, Tetrahedron, Jul. 9, 1999, pp. 8377-8384, vol. 55 Issue 28.

Latif et al, Cleavage of Xanthene Ethers a New Route to 9-Substituted Xanthenes, Canadian Journal of Chemistry, vol. 42 (1964), pp. 1736-1740.

Luning, et al., Bimacrocyiic 1,10-Phenanthroline Cyclophanes, Chemische Beri, 1990, pp. 643-645, vol. 123 Issue 3.

PCT International Search Report, dated Oct. 4, 2018, for PCT Int'l Appln. No. PCT/IB2018/054588.

PCT International Search Report; dated Nov. 9, 2018, for PCT Intl Appl'n. No. PCT/IB2018/054585.

PCT International Search Report, dated Jul. 17, 2018, for PCT Int'l Appln. No. PCT/IB2018/053669.

PCT International Search Report, dated May 24, 2019, for PCT Int'l Appln. No. PCT/IB2019/051582.

Reck, et al., Enantiopure Chiral Chiral Concave 1,10-Phenanthrolines, European Journal of Organic Chemistry, 2016, pp. 1119-1131, vol. 2016 Issue 6.

\* cited by examiner

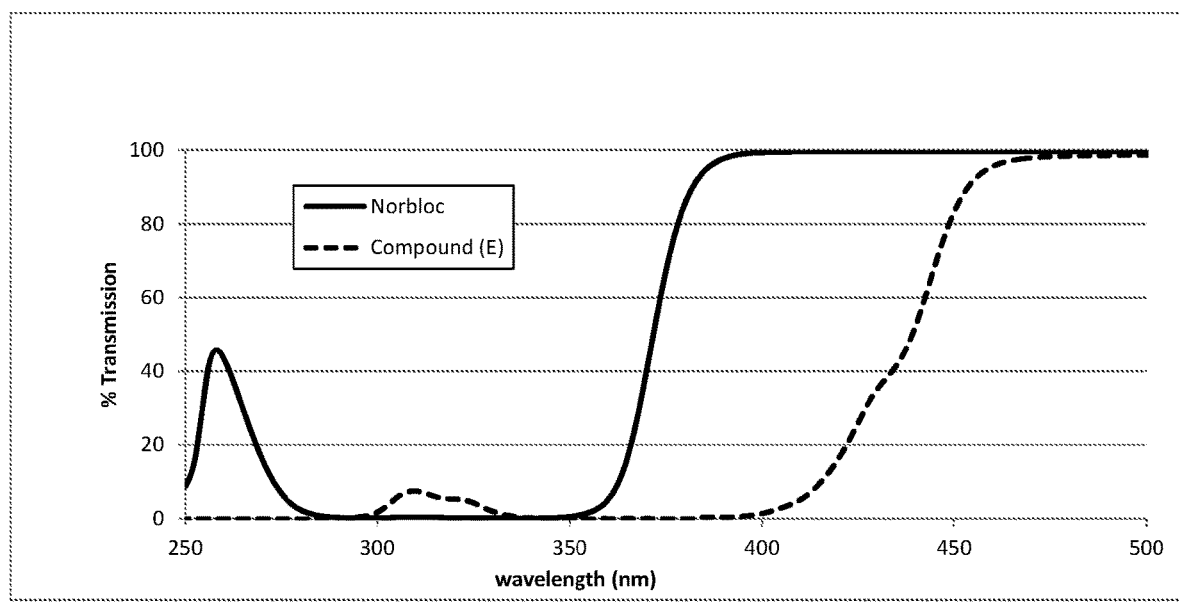
FIG. 1 – Transmission Spectra of Norbloc® and Compound (E) in 0.2 mM methanol solutions

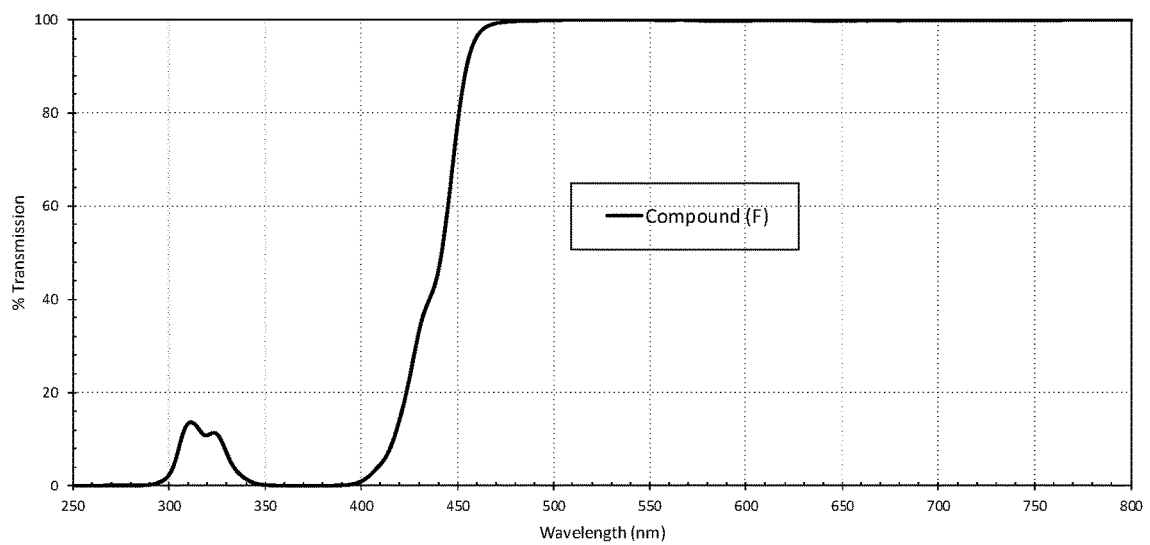
FIG. 2 – Transmission Spectra of Compound (F) in 0.2 mM dichloromethane solution

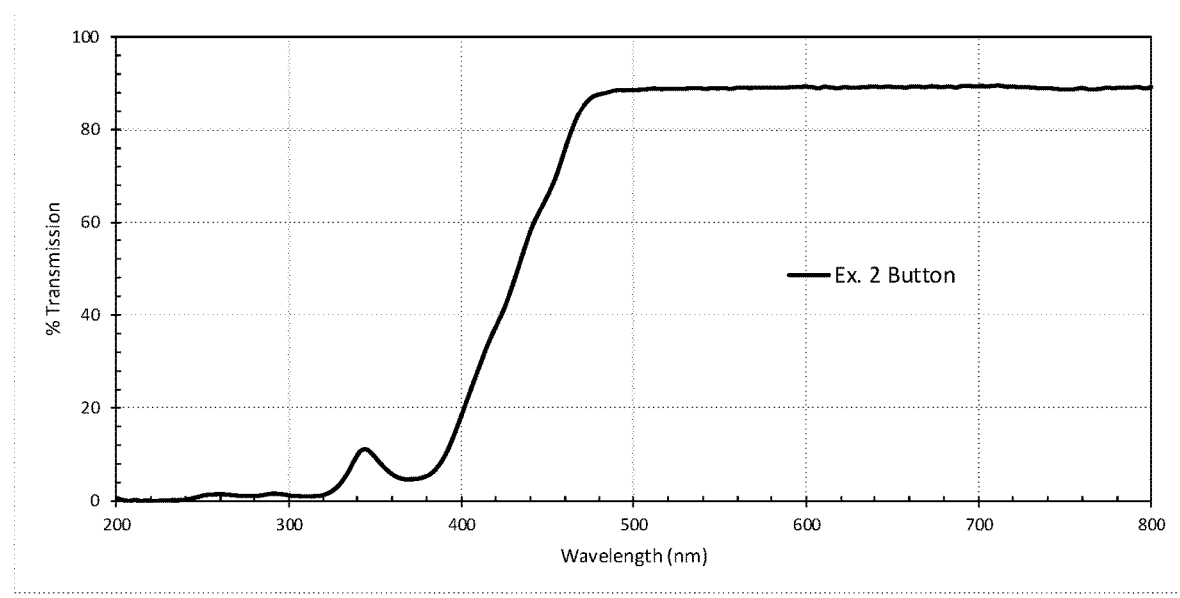
FIG. 3 – Transmission Spectra of an ethylene glycol swollen polyHEMA network containing polymerized Compound (F)

HYDROXYPHENYL NAPHTHOTRIAZOLES AS POLYMERIZABLE BLOCKERS OF HIGH ENERGY LIGHT

RELATED APPLICATIONS

This application is a continuation of U.S. patent application Ser. No. 15/979,619, filed May 15, 2018, now U.S. Pat. No. 10,526,296, which claims priority to U.S. Provisional Patent Application No. 62/527,106, filed Jun. 30, 2017, which is incorporated herein by reference in its entirety.

FIELD OF THE INVENTION

The invention relates to high energy light blockers. More particularly, the invention pertains to hydroxyphenyl naphthotriazole derivatives with polymerizable functionality that block high energy light (including ultraviolet light). The high energy light blockers may be used in polymeric articles, including biomedical devices, such as ophthalmic devices.

BACKGROUND OF THE INVENTION

High energy radiation from the sun, such as UV and high-energy visible light, is known to be responsible for cellular damage. While most of the radiation below 280 nm in wavelength is absorbed by the earth's atmosphere, photons possessing wavelengths ranging between 280 and 400 nm have been associated with several ocular disorders including corneal degenerative changes, and age-related cataract and macular degeneration. (See Statement on Ocular Ultraviolet Radiation Hazards in Sunlight, American Optometric Association, Nov. 10, 1993). The human cornea absorbs radiation up to 320 nm in wavelength (30% transmission) (Doutch, J. J., Quantock, A. J., Joyce, N. C., Meek, K. M, *Biophys. J,* 2012, 102, 1258-1264), but is inefficient in protecting the back of the eye from radiation ranging from 320 to 400 nm in wavelength.

High energy visible light in the range of 400 to 450 nm is emiited by many types of electronic device, including smartphones, computer screens, and televisions. With the widespread and increasing use of electronic devices, such high energy visible light has come under recent scrutiny for its potential negative effects, for instance on health, eye strain, and its disruption of the circadian rhythm.

Contact lens standards define the upper UV radiation wavelength at 380 nm. The current Class I UV blocking criteria defined by the American Optometric Association require >99% of the radiation between 280 and 315 nm (UV B) and >90% of the 316 to 380 nm (UV A) radiation to be absorbed by the contact lens. While the criteria effectively address protection of the cornea (<1% UV B transmittance), there is little attention paid to the lower energy UV radiation (>380<400 nm) and the high energy visible radiation associated with retinal damage (Ham, W. T, Mueller, H. A., Sliney, D. H. *Nature* 1976; 260(5547):153-5), eye strain, and disruption of sleep.

Polymerizable compounds possessing appropriate chromophores, if used as ophthalmic device monomers, can help protect the cornea, as well as the interior cells in the ocular environment, from degradation caused by high energy light. Such materials may also mitigate eye strain and the circadian rhythm disruption that may result from exposure to high energy visible light such as emitted by electronic devices.

SUMMARY OF THE INVENTION

The invention relates to high energy light absorbers with hydroxyphenyl naphthotriazole structures having a high absorption (low transmission) over the wavelength range of at least 200-400 nm, while substantially transmitting (e.g., greater than 80% transmission) at wavelengths of about 450 nm or longer. The materials are therefore effective at blocking high energy light, such as UV (UVA and UVB) and high energy visible light (e.g., up to 425 nm or greater).

In one aspect, therefore, the invention provides a compound of formula I:

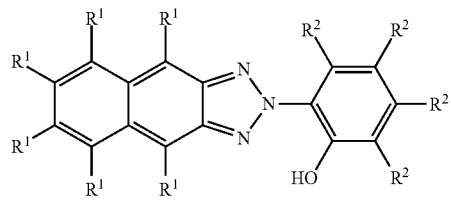

Formula I wherein:

$R^1$ at each occurrence is independently H, halo (e.g., chloro), $C_1$-$C_6$ alkyl, $C_3$-$C_{12}$ cycloalkyl, aryl, or aryl-$C_1$-$C_6$-alkyl;

at least one $R^2$ is a group of formula $R_g$-L, wherein $R_g$ is a polymerizable group and L is a linking group, and the remaining $R^2$ are independently at each occurrence $R_g$-L, H, $C_1$-$C_6$ alkyl, $C_3$-$C_{12}$ cycloalkyl, aryl, or aryl-$C_1$-$C_6$-alkyl, wherein L at each occurrence is independently —[$CH_2$]$_m$—Y—[$CH_2$]$_n$—, wherein m is a number from 1 to 6, n is a number from 1 to 6, Y is O, S, C(=O)O, $NR^3$, or C(=O)$NR^3$, and $R^3$ is H or $C_1$-$C_4$ alkyl; and wherein each alkyl, cycloalkyl, and aryl group is unsubstituted or substituted.

The invention also provides an ophthalmic device comprising the compound of formula I as a free radical reaction product.

The invention further provides a method for making an ophthalmic device. The method comprises: (a) providing a reactive mixture containing a compound of formula I, one or more monomers suitable for use in making an ophthalmic device, and a radical initiator; and (b) polymerizing the reactive mixture to form the ophthalmic device.

The invention also provides a contact lens comprising a hydrogel polymer formed by polymerizing one or more monomers suitable for use in making the hydrogel polymer, and copolymerizing an effective amount of a compound of formula I.

BRIEF DESCRIPTION OF DRAWINGS

FIG. 1 shows transmission spectra of Norbloc® and exemplary Compound (E) in 0.2 mM methanol solutions.

FIG. 2 shows a transmission spectrum of exemplary Compound (F) in 0.2 mM dichloromethane solution.

FIG. 3 shows a transmission spectrum of an ethylene glycol swollen polyHEMA network containing polymerized Compound (F).

DETAILED DESCRIPTION OF THE INVENTION

It is to be understood that the invention is not limited to the details of construction or process steps set forth in the following description. The invention is capable of other embodiments and of being practiced or being carried out in various ways using the teaching herein.

As noted above, the invention provides high energy light blockers. The high energy light blockers contain hydroxyphenyl naphthotriazole core structures. The materials also contain polymerizable functionality. Thus, materials according to the invention have been found to block high energy light in the wavelength range of at least from 200 to 400 nm, or from 200 to 410 nm, or 200 to 425 nm, or 200 to 450 nm. Advantageously, the materials exhibit a transmission cut-off (e.g., they absorb 20 percent or less) at visible wavelengths longer than about 450 nm. Thus, the materials may be used to block UVA, UVB, and some wavelengths of high energy visible light, while transmitting in the visible spectrum, making them strong Class I and Class II UV absorbers that are well suited for use in ophthalmic applications.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula $[***]_n$, is used to depict the number of repeating units in a polymer's chemical formula, the formula should be interpreted to represent the number average molecular weight of the macromolecule.

The term "individual" includes humans and vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular lenses and contact lenses. The biomedical devices may be ophthalmic devices, particularly contact lenses, most particularly contact lenses made from silicone hydrogels or conventional hydrogels.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light blocking, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The biomedical devices, ophthalmic devices, and lenses of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyl lactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result, and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers, still containing polymerizable groups capable of undergoing further reaction to form a polymer.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N,N-dimethylacrylamide ("DMA") or vinyl acetate. U.S. Pat. Nos. 4,436,887, 4,495, 313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, falcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

The terms "reactive mixture" and "reactive monomer mixture" refer to the mixture of components (both reactive and non-reactive) which are mixed together and when subjected to polymerization conditions form the conventional or silicone hydrogels of the present invention as well as contact lenses made therefrom. The reactive monomer mixture may comprise reactive components such as the monomers, macromers, prepolymers, cross-linkers, and initiators, additives such as wetting agents, release agents, polymers, dyes, light absorbing compounds such as UV absorbers, pigments, dyes and photochromic compounds, any of which may be reactive or non-reactive but are capable of being retained within the resulting biomedical device, as well as pharmaceutical and nutraceutical compounds, and any diluents. It will be appreciated that a wide range of additives may be added based upon the biomedical device which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a hydrogel contact lens comprising at least one silicone containing component. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

As used herein, the term "alkyl" refers to an unsubstituted or substituted linear or branched alkyl group containing the indicated number of carbon atoms. If no number is indicated, then alkyl (optionally including any substituents on alkyl) may contain 1 to 16 carbon atoms. Preferably, the alkyl group contains 1 to 10 carbon atoms, alternatively 1 to 7 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, amido, carbamate, carbonate, halogen, phenyl, benzyl, and combinations thereof. "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —$CF_3$— or —$CF_2CF_3$—. "Haloalkylene" means a divalent haloalkyl group, such as —$CH_2CF_2$—.

"Cycloalkyl" refers to an unsubstituted or substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an unsubstituted or substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, amido, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings.

Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —CH$_2$CH$_2$NH—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected R$^A$ groups (where R$^A$ is as defined in formula A options (b)-(i)) to complete their valence.

"Silyl" refers to a structure of formula R$_3$Si— and "siloxy" refers to a structure of formula R$_3$Si—O—, where each R in silyl or siloxy is independently selected from trimethylsiloxy, C$_1$-C$_8$ alkyl (preferably C$_1$-C$_3$ alkyl, more preferably ethyl or methyl), and C$_3$-C$_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[CH$_2$CH$_2$O]$_p$— or CH$_3$O—[CH$_2$CH$_2$O]$_p$—). Examples of alkyleneoxy include polymethyleneoxy, polyethyleneoxy, polypropyleneoxy, polybutyleneoxy, and poly(ethyleneoxy-co-propyleneoxy).

"Oxaalkylene" refers to an alkylene group as defined above where one or more non-adjacent CH$_2$ groups have been substituted with an oxygen atom, such as —CH$_2$CH$_2$OCH(CH$_3$)CH$_2$—. "Thiaalkylene" refers to an alkylene group as defined above where one or more non-adjacent CH$_2$ groups have been substituted with a sulfur atom, such as —CH$_2$CH$_2$SCH(CH$_3$)CH$_2$—.

The term "linking group" refers to a moiety that links the polymerizable group to the parent molecule. The linking group may be any moiety that does not undesirably interfere with the polymerization of the compound of which it is a part. For instance, the linking group may be a bond, or it may comprise one or more alkylene, haloalkylene, amide, amine, alkyleneamine, carbamate, carboxylate (—CO$_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF$_2$—, —OCF$_2$CF$_2$—, —OCF$_2$CH$_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, CH$_3$O-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include C$_1$-C$_8$ alkylene (preferably C$_2$-C$_6$ alkylene) and C$_1$-C$_8$ oxaalkylene (preferably C$_2$-C$_6$ oxaalkylene), each of which is optionally substituted with 1 or 2 groups independently selected from hydroxyl and siloxy. Preferred linking groups also include carboxylate, amide, C$_1$-C$_8$ alkylene-carboxylate-C$_1$-C$_8$ alkylene, or C$_1$-C$_8$ alkylene-amide-C$_1$-C$_8$ alkylene.

When the linking group is comprised of combinations of moieties as described above (e.g., alkylene and cycloalkylene), the moieties may be present in any order. For instance, if in Formula E below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg) to which the linking group is attached. For example, if in Formula E, L and L$^2$ are indicated as both being alkylene-cycloalkylene, then Rg-L is preferably Rg-alkylene-cycloalkylene- and -L$^2$-Rg is preferably -cycloalkylene-alkylene-Rg.

The terms "high energy light blocker" or "high energy light absorber" refer to chemical materials which block ultraviolet light and, in some cases, also block high energy visible light. If the amount of a material's blocking is indicated as a percentage for a particular wavelength range, it is to be understood that the material exhibits the percent blocking at all wavelengths within that range. Percent blocking at a particular wavelength can be determined from the material's transmission spectrum, where blocking=100−percent transmission (% T). Preferred materials block at least 60%, or at least 70%, or at least 80%, or at least 85%, or at least 90%, or at least 95% of high energy light at all wavelengths within the indicated high energy light range, while significantly transmitting light in the visible range, thus allowing the materials to be used in ophthalmic applications. Preferred materials block 20% or less, preferably 10% or less, more preferably 5% or less in the visible spectrum, for instance from 450 nm to 700 nm.

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

As noted above, in one aspect, the invention provides hydroxyphenyl naphthotriazole materials that function as high energy light blockers. The hydroxyphenyl naphthotriazole materials are of the formula I:

Formula I

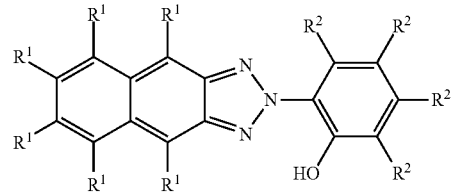

wherein:

R¹ at each occurrence is independently H, halo, $C_1$-$C_6$ alkyl, $C_3$-$C_2$ cycloalkyl, aryl (e.g., phenyl), or aryl-$C_1$-$C_6$-alkyl (e.g., benzyl); at least one R² is a group of formula $R_g$-L, wherein $R_g$ is a polymerizable group and L is a linking group, and the remaining R² are independently at each occurrence $R_g$-L, H, $C_1$-$C_6$ alkyl, $C_3$-$C_2$ cycloalkyl, aryl, or aryl-$C_1$-$C_6$-alkyl, wherein L at each occurrence is independently —[$CH_2$]$_m$—Y—[$CH_2$]$_n$—, wherein m is a number from 1 to 6, n is a number from 1 to 6, Y is O, S, C(=O)O, $NR^3$, or C(=O)$NR^3$, and R³ is H or $C_1$-$C_4$ alkyl; and wherein each alkyl, cycloalkyl, and aryl group is unsubstituted or substituted. Hydroxyphenyl naphthotriazoles of Formula I preferably contain one or two $R_g$-L groups. More preferably, the materials contain one $R_g$-L group. The formula I structure (and its various sub-structures as described below) encompasses salts of the hydroxyphenyl naphthotriazoles.

Formula I-1. Hydroxyphenyl naphthotriazoles of formula I may include materials of formula I-1, which are hydroxyphenyl naphthotriazoles of formula I wherein R¹ is H, chloro, $C_1$-$C_4$ alkyl, phenyl, or benzyl. Preferred materials of formula I-1 also include those wherein each R¹ is hydrogen.

I-2. Hydroxyphenyl naphthotriazoles of formulae I and I-1 may include materials of formula I-2, which are hydroxyphenyl naphthotriazoles of formula I or I-1 wherein R² at each occurrence is independently H, $C_1$-$C_4$ alkyl, phenyl, benzyl, or $R_g$-L. Preferred materials of formula I-2 include those wherein one R² is $R_g$-L and the remaining R² are independently hydrogen or $C_1$-$C_6$ alkyl. Preferred materials of formula I-2 also include those wherein one R² is $R_g$-L and the remaining R² are each hydrogen.

I-3. Hydroxyphenyl naphthotriazoles of formulae I, I-1, and I-2 may include materials of formula I-3, which are hydroxyphenyl naphthotriazoles of formula I, I-1, or I-2 wherein Rg (the polymerizable group) at each occurrence independently comprises styryl, vinyl carbonate, vinyl ether, vinyl carbamate, N-vinyl lactam, N-vinylamide, (meth)acrylate, or (meth)acrylamide. The polymerizable group allows the hydroxyphenyl naphthotriazole materials of the invention to form covalent bonds when reacted with monomers, crosslinking agents, and other components generally used in making polymeric devices. The compatibility of the hydroxyphenyl naphthotriazoles with the reactive mixture can be controlled via the selection of the polymerizable group (and the linking group). Preferred Rg groups include (meth)acrylate or (meth)acrylamide. A more preferred Rg group is methacrylate.

I-4. Hydroxyphenyl naphthotriazoles of formulae I, I-1, I-2, and I-3 may include materials of formula I-4, which are hydroxyphenyl naphthotriazoles of formula I, I-1, I-2, or I-3 wherein the linking group comprises $C_1$-$C_4$ alkylene-carboxylate-$C_1$-$C_4$ alkylene or $C_1$-$C_4$ alkylene-amide-$C_1$-$C_4$ alkylene. Particularly preferred linking groups are —$CH_2CH_2$—NH—C(=O)—$CH_2CH_2$— and —$CH_2CH_2$—O—C(=O)—$CH_2CH_2$—.

I-5. Hydroxyphenyl naphthotriazoles of formulae I, I-1, I-2, I-3, and I-4 may include materials of formula I-5, which are hydroxyphenyl naphthotriazoles of formula I, I-1, I-2, I-3, or I-4 having the structure:

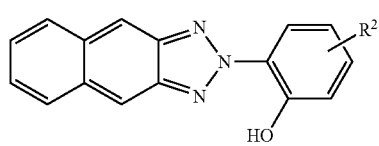

Formula I-5 wherein R² is $R_g$-L, wherein Rg is a polymerizable group and L is —[$CH_2$]$_m$—Y—[$CH_2$]$_n$—, m is a number from 1 to 6, n is a number from 1 to 6, Y is O, S, C(=O)O, $NR^3$, or C(=O)$NR^3$, and R³ is H or $C_1$-$C_4$ alkyl. Preferably, Rg is as specified in formula I-3 and L is as specified in formula I-4.

I-6. Hydroxyphenyl naphthotriazoles of formulae I, I-1, I-2, I-3, I-4, and I-5 may include materials of formula I-6, which are hydroxyphenyl naphthotriazoles of formula I, I-1, I-2, I-3, I-4, or I-5 having the structure:

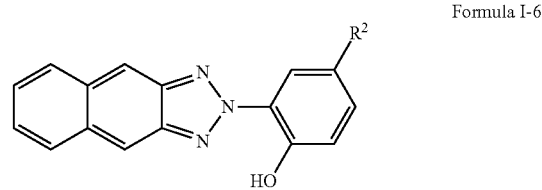

Formula I-6 wherein R² is $R_g$-L, wherein Rg is a polymerizable group and L is —[$CH_2$]$_m$—Y—[$CH_2$]$_n$—, m is a number from 1 to 6, n is a number from 1 to 6, Y is O, S, C(=O)O, $NR^3$, or C(=O)$NR^3$, and R³ is H or $C_1$-$C_4$ alkyl. Preferably, Rg is as specified in formula I-3 and L is as specified in formula I-4.

Examples of Hydroxyphenyl naphthotriazoles suitable for use in the invention include, but are not limited to, compounds listed in Table 1.

TABLE 1

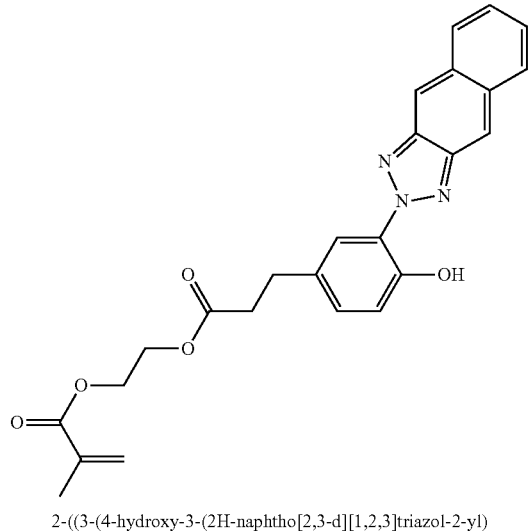

2-((3-(4-hydroxy-3-(2H-naphtho[2,3-d][1,2,3]triazol-2-yl)phenyl)propanoyl)oxy)ethyl methacrylate TABLE 1-continued

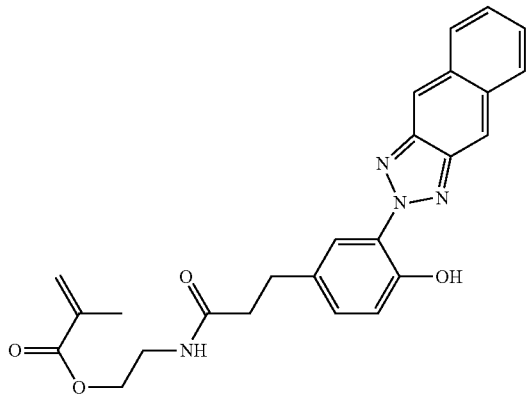

2-(3-(4-hydroxy-3-(2H-naphtho[2,3-d][1,2,3]triazol-2-yl)
phenyl)propanamido)ethyl methacrylate Compounds of formula I may be prepared as described in the Examples below, as well as relevant literature procedures known to those of skill in the art.

The present invention encompasses compounds that may be used as precursors from which the compounds of formula I may be prepared. These include:

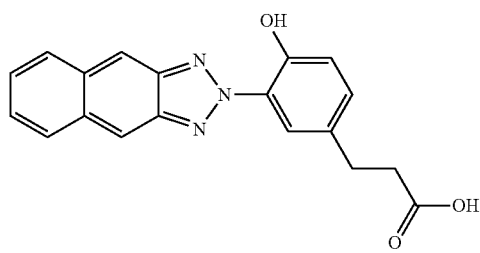

3-(4-Hydroxy-3-(2H-naphtho[2,3-d][1,2,3]triazol-2-yl)phenyl)propanoic acid (Compound D)

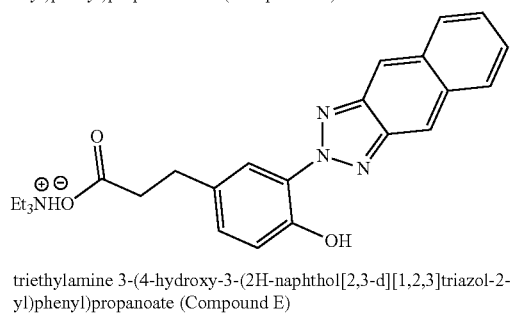

triethylamine 3-(4-hydroxy-3-(2H-naphthol[2,3-d][1,2,3]triazol-2-yl)phenyl)propanoate (Compound E)

As discussed above, the hydroxyphenyl naphthotriazoles of formula I are effective at blocking high energy light in at least the 200-400 nm range while transmitting visible wavelengths longer than about 450 nm. The hydroxyphenyl naphthotriazoles of the invention may block at least 90% or light, or at least 95% of light, in the 200 to 400 nm range, and at least 60% of light in the 400 to 425 nm range. Because of their selective high energy light blocking properties, the compositions are well suited for use in ophthalmic devices. In such devices, the compositions may block harmful high energy radiation, therefore protecting the eye from damage or strain, while allowing transmission of visible light.

The hydroxyphenyl naphthotriazoles of formula I may be included in reactive mixtures to form an ophthalmic device. Generally, the hydroxyphenyl naphthotriazoles can be present in any amount up to the limit of their solubility. For instance, the hydroxyphenyl naphthotriazoles may be present in an amount in the range of about 0.1% to about 10% by weight, or from about 0.5 to about 5% by weight, or from about 0.75% to about 4% by weight. The upper limit is typically determined by the solubility of the compound with other comonomers and or diluents in the reactive monomer mix.

A variety of ophthalmic devices containing the hydroxyphenyl naphthotriazoles of the invention may be prepared, including hard contact lenses, soft contact lenses, corneal onlays, corneal inlays, intraocular lenses, or overlay lenses. Preferably, the ophthalmic device is a soft contact lens, which may be made from conventional or silicone hydrogel formulations.

Ophthalmic devices may be prepared by polymerizing a reactive mixture containing the hydroxyphenyl naphthotriazole, one or more monomers suitable for making the desired ophthalmic device, and optional components. Thus, the reactive mixture may include, in addition to a hydroxyphenyl naphthotriazole compound as described above, one or more of: hydrophilic components, hydrophobic components, silicone-containing components, wetting agents such as polyamides, crosslinking agents, and further components such as diluents and initiators.

Hydrophilic Components

Examples of suitable families of hydrophilic monomers include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth) acrylamide, N-(3-hydroxybutyl) (meth)acrylamide, N-(4-hydroxybutyl) (meth)acrylamide, 2-aminoethyl (meth) acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth) acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-β-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl) amino]propyl]-3-sulfo-, inner salt (SBT), 3,5-Dioxa-8-aza- 4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and 3-((3-(methacryloyloxy)propyl)dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof.

Non-limiting examples of hydrophilic O-vinyl carbamates and O-vinyl carbonates monomers include N-2-hydroxyethyl vinyl carbamate and N-carboxy-β-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of about 0.1 to about 80 weight percent, including in the range of about 5 to about 65 weight percent, and in the range of about 10 to about 45 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, or mixtures of the foregoing; one or more optionally repeating siloxane units; and one or more linking groups connecting the polymerizable groups to the siloxane units.

Formula A. The silicone-containing component may comprise one or more polymerizable compounds of Formula A:

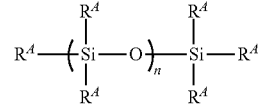

Formula A wherein:
at least one $R^A$ is a group of formula $R_g$-L- wherein $R_g$ is a polymerizable group and L is a linking group, and the remaining $R^A$ are each independently:
(a) $R_g$-L-,
(b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
(c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof,
(d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
(e) halo, (f) alkoxy, cyclic alkoxy, or aryloxy,
(g) siloxy,
(h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or
(i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^4$ substituents and if different $R^4$ substituents are present, the n groups may be in random or block configuration.

In Formula A, three $R^4$ may each comprise a polymerizable group, alternatively two $R^4$ may each comprise a polymerizable group, or alternatively one $R^4$ may comprise a polymerizable group. Formula B. The silicone-containing component of formula A may be a mono-functional polymerizable compound of formula B:

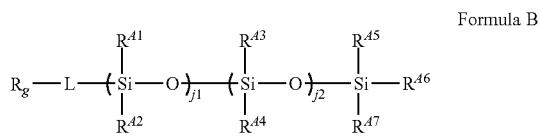

Formula B wherein:
Rg is a polymerizable group;
L is a linking group;
j1 and j2 are each independently whole numbers from 0 to 220, provided that the sum of j1 and j2 is from 1 to 220;
$R^{41}$, $R^{42}$, $R^{43}$, $R^{44}$, $R^{45}$, and $R^{47}$ are independently at each occurrence $C_1$-$C_6$ alkyl, $C_3$-$C_{12}$ cycloalkyl, $C_1$-$C_6$ alkoxy, $C_4$-$C_{12}$ cyclic alkoxy, alkoxy-alkyleneoxy-alkyl, aryl (e.g., phenyl), aryl-alkyl (e.g., benzyl), haloalkyl (e.g., partially or fully fluorinated alkyl), siloxy, fluoro, or combinations thereof, wherein each alkyl in the foregoing groups is optionally substituted with one or more hydroxy, amino, amido, oxa, carboxy, alkyl carboxy, carbonyl, alkoxy, carbamate, carbonate, halo, phenyl, or benzyl, each cycloalkyl is optionally substituted with one or more alkyl, hydroxy, amino, amido, oxa, carbonyl, alkoxy, carbamate, carbonate, halo, phenyl, or benzyl and each aryl is optionally substituted with one or more alkyl, hydroxy, amino, amido, oxa, carboxy, alkyl carboxy, carbonyl, alkoxy, carbamate, carbonate, halo, phenyl, or benzyl; and
$R^{46}$ is siloxy, $C_1$-$C_8$ alkyl (e.g., $C_1$-$C_4$ alkyl, or butyl, or methyl), or aryl (e.g., phenyl), wherein alkyl and aryl may optionally be substituted with one or more fluorine atoms.

Formula B-1. Compounds of formula B may include compounds of formula B-1, which are compounds of formula B wherein j1 is zero and j2 is from 1 to 220, or j2 is from 1 to 100, or j2 is from 1 to 50, or j2 is from 1 to 20, or j2 is from 1 to 5, or j2 is 1.

B-2. Compounds of formula B may include compounds of formula B-2, which are compounds of formula B wherein j1 and j2 are independently from 4 to 100, or from 4 to 20, or from 4 to 10, or from 24 to 100, or from 10 to 100.

B-3. Compounds of formulae B, B-1, and B-2 may include compounds of formula B-3, which are compounds of formula B, B-1, or B-2 wherein $R^{41}$, $R^{42}$, $R^{43}$, and $R^{44}$ are independently at each occurrence $C_1$-$C_6$ alkyl or siloxy. Preferred alkyl are $C_1$-$C_3$ alkyl, or more preferably, methyl. Preferred siloxy is trimethylsiloxy.

B-4. Compounds of formulae B, B-1, B-2, and B-3 may include compounds of formula B-4, which are compounds of formula B, B-1, B-2, or B-3 wherein $R^{45}$ and $R^{47}$ are independently alkoxy-alkyleneoxy-alkyl, preferably they are independently a methoxy capped polyethyleneoxyalkyl of formula $CH_3O$—$[CH_2CH_2O]_p$—$CH_2CH_2CH_2$, wherein p is a whole number from 1 to 50.

B-5. Compounds of formulae B, B-1, B-2, and B-3 may include compounds of formula B-5, which are compounds of formula B, B-1, B-2, or B-3 wherein $R^{45}$ and $R^{47}$ are independently siloxy, such as trimethylsiloxy.

B-6. Compounds of formulae B, B-1, B-2, and B-3 may include compounds of formula B-6, which are compounds of formula B, B-1, B-2, or B-3 wherein $R^{45}$ and $R^{47}$ are independently $C1$-$C_6$ alkyl, alternatively $C_1$-$C_4$ alkyl, or alternatively, butyl or methyl.

B-7. Compounds of formulae B, B-1, B-2, B-3, B-4, B-5, and B-6 may include compounds of formula B-7, which are compounds of formula B, B-1, B-2, B-3, B-4, B-5, or B-6 wherein $R^{46}$ is $C_1$-$C_8$ alkyl, preferably $C_1$-$C_6$ alkyl, more preferably $C_1$-$C_4$ alkyl (for example methyl, ethyl, n-propyl, or n-butyl). More preferably $R^{46}$ is n-butyl.

B-8. Compounds of formulae B, B-1, B-2, B-3, B-4, B-5, B-6, and B-7, may include compounds of formula B-8, which are compounds of formula B, B-1, B-2, B-3, B-4, B-5, B-6, or B-7 wherein Rg comprises styryl, vinyl carbonate, vinyl ether, vinyl carbamate, N-vinyl lactam, N-vinylamide, (meth)acrylate, or (meth)acrylamide. Preferably, Rg comprises (meth)acrylate, (meth)acrylamide, or styryl. More preferably, Rg comprises (meth)acrylate or (meth)acrylamide. When Rg is (meth)acrylamide, the nitrogen group may be substituted with $R^{49}$, wherein $R^{49}$ is H, $C_1$-$C_8$ alkyl (preferably $C_1$-$C_4$ alkyl, such as n-butyl, n-propyl, methyl or ethyl), or $C_3$-$C_8$ cycloalkyl (preferably $C_5$-$C_6$ cycloalkyl), wherein alkyl and cycloalkyl are optionally substituted with one or more groups independently selected from hydroxyl, amide, ether, silyl (e.g., trimethylsilyl), siloxy (e.g., trimethylsiloxy), alkyl-siloxanyl (where alkyl is itself optionally substituted with fluoro), aryl-siloxanyl (where aryl is itself optionally substituted with fluoro), and silyl-oxaalkylene- (where the oxaalkylene is itself optionally substituted with hydroxyl).

B-9. Compounds of formulae B, B-1, B-2, B-3, B-4, B-5, B-6, B-7, and B-8 may include compounds of formula B-9, which are compounds of formula B, B-1, B-2, B-3, B-4, B-5, B-6, B-7, or B-8 wherein the linking group comprises alkylene (preferably $C_1$-$C_4$ alkylene), cycloalkylene (preferably $C_5$-$C_6$ cycloalkylene), alkyleneoxy (preferably ethyleneoxy), haloalkyleneoxy (preferably haloethyleneoxy), amide, oxaalkylene (preferably containing 3 to 6 carbon atoms), siloxanyl, alkylenesiloxanyl, carbamate, alkyleneamine (preferably $C_1$-$C_6$ alkyleneamine), or combinations of two or more thereof, wherein the linking group is optionally substituted with one or more substituents independently selected from alkyl, hydroxyl, ether, amine, carbonyl, siloxy, and carbamate.

B-10. Compounds of formulae B, B-1, B-2, B-3, B-4, B-5, B-6, B-7, B-8, and B-9 may include compounds of formula B-10, which are compounds of formula B, B-1, B-2, B-3, B-4, B-5, B-6, B-7, B-8, or B-9 wherein the linking group is alkylene-siloxanyl-alkylene-alkyleneoxy-, or alkylene-siloxanyl-alkylene-[alkyleneoxy-alkylene-siloxanyl]$_q$-alkyleneoxy-, where q is from 1 to 50.

B-11. Compounds of formulae B, B-1, B-2, B-3, B-4, B-5, B-6, B-7, B-8, and B-9 may include compounds of formula B-11, which are compounds of formula B, B-1, B-2, B-3, B-4, B-5, B-6, B-7, B-8, or B-9 wherein the linking group is C1-$C_6$ alkylene, preferably $C_1$-$C_3$ alkylene, more preferably n-propylene.

B-12. Compounds of formulae B, B-1, B-2, B-3, B-4, B-5, B-6, B-7, B-8, and B-9 may include compounds of formula B-12, which are compounds of formula B, B-1, B-2, B-3, B-4, B-5, B-6, B-7, B-8, or B-9 wherein the linking group is alkylene-carbamate-oxaalkylene. Preferably, the linking group is $CH_2CH_2N(H)$—$C(=O)$—$O$—$CH_2CH_2$—$O$—$CH_2CH_2CH_2$.

B-13. Compounds of formulae B, B-1, B-2, B-3, B-4, B-5, B-6, B-7, B-8, and B-9 may include compounds of formula B-13, which are compounds of formula B, B-1, B-2, B-3, B-4, B-5, B-6, B-7, B-8, or B-9 wherein the linking group is oxaalkylene. Preferably, the linking group is $CH_2CH_2$—$O$—$CH_2CH_2CH_2$.

B-14. Compounds of formulae B, B-1, B-2, B-3, B-4, B-5, B-6, B-7, B-8, and B-9 may include compounds of formula B-14, which are compounds of formula B, B-1, B-2, B-3, B-4, B-5, B-6, B-7, B-8, or B-9 wherein the linking group is alkylene-[siloxanyl-alkylene]$_q$-, where q is from 1 to 50. An example of such a linking group is: —$(CH_2)_3$—[Si-$(CH_3)_2$—O—$Si(CH_3)_2$—$(CH_2)_2]_q$—.

B-15. Compounds of formulae B, B-1, B-2, B-3, B-4, B-5, B-6, B-7, B-8, and B-9 may include compounds of formula B-15, which are compounds of formula B, B-1, B-2, B-3, B-4, B-5, B-6, B-7, B-8, or B-9 wherein the linking group is alkyleneoxy-carbamate-alkylene-cycloalkylene-carbamate-oxaalkylene, wherein cycloalkylene is optionally substituted with or 1, 2, or 3 independently selected alkyl groups (preferably C1-C3 alkyl, more preferably methyl). An example of such a linking group is —[$OCH_2CH_2]_q$—OC(=O)—NH—$CH_2$—[1,3-cyclohexylene]-NHC (=O)O—$CH_2CH_2$—O—$CH_2CH_2$—, wherein the cyclohexylene is substituted at the 1 and 5 positions with 3 methyl groups.

B-16. Compounds of formulae B, B-1, B-2, B-3, B-4, B-5, B-6, B-7, B-8, and B-9 may include compounds of formula B-16, which are compounds of formula B, B-1, B-2, B-3, B-4, B-5, B-6, B-7, B-8, or B-9 wherein Rg comprises styryl and the linking group is alkyleneoxy wherein each alkyleneoxy in alkyleneoxy is independently optionally substituted with hydroxyl. An example of such a linking group is —O—$(CH_2)_3$—. Another example of such a linking group is —O—$CH_2CH(OH)CH_2$—O—$(CH_2)_3$—.

B-17. Compounds of formulae B, B-1, B-2, B-3, B-4, B-5, B-6, B-7, B-8, and B-9 may include compounds of formula B-17, which are compounds of formula B, B-1, B-2, B-3, B-4, B-5, B-6, B-7, B-8, or B-9 wherein Rg comprises styryl and the linking group is alkyleneamine. An example of such a linking group is —NH—$(CH_2)_3$—.

B-18. Compounds of formulae B, B-1, B-2, B-3, B-4, B-5, B-6, B-7, B-8, and B-9 may include compounds of formula B-18, which are compounds of formula B, B-1, B-2, B-3, B-4, B-5, B-6, B-7, B-8, or B-9 wherein the linking group is oxaalkylene optionally substituted with hydroxyl, siloxy, or silyl-alkyleneoxy (where the alkyleneoxy is itself optionally substituted with hydroxyl). An example of such a linking group is —$CH_2CH(G)CH_2$—O—$(CH_2)_3$—, wherein G is hydroxyl. In another example, G is $R_3SiO$— wherein two R groups are trimethylsiloxy and the third is $C_1$-$C_8$ alkyl (preferably $C_1$-$C_3$ alkyl, more preferably methyl) or the third is $C_3$-$C_8$ cycloalkyl. In a further example, G is $R_3Si$—$(CH_2)_3$—O—$CH_2CH(OH)CH_2$—O—, wherein two R groups are trimethylsiloxy and the third is $C_1$-$C_8$ alkyl (preferably $C_1$-$C_3$ alkyl, more preferably methyl) or $C_3$-$C_8$ cycloalkyl. In a still further example, G is a polymerizable group, such as (meth)acrylate. Such compounds may function as crosslinkers.

B-19. Compounds of formulae B, B-1, B-2, B-3, B-4, B-5, B-6, B-7, B-8, and B-9 may include compounds of formula B-19, which are compounds of formula B, B-1, B-2, B-3, B-4, B-5, B-6, B-7, B-8, or B-9 wherein Rg comprises styryl and the linking group is amine-oxaalkylene optionally substituted with hydroxyl. An example of such a linking group is —NH—$CH_2CH(OH)CH_2$—O—$(CH_2)_3$—.

B-20. Compounds of formulae B, B-1, B-2, B-3, B-4, B-5, B-6, B-7, B-8, and B-9 may include compounds of formula B-20, which are compounds of formula B, B-1, B-2, B-3, B-4, B-5, B-6, B-7, B-8, or B-9 wherein Rg comprises styryl and the linking group is alkyleneoxy-carbamate-oxaalkylene. An example of such a linking group is —O—$(CH_2)_2$—$N(H)C(=O)O$—$(CH_2)_2$—O—$(CH_2)_3$—.

B-21. Compounds of formulae B, B-1, B-2, B-3, B-4, B-5, B-6, B-7, B-8, and B-9 may include compounds of formula B-21, which are compounds of formula B, B-1, B-2, B-3, B-4, B-5, B-6, B-7, B-8, or B-9 wherein the linking group is alkylene-carbamate-oxaalkylene. An example of such a linking group is —$(CH_2)_2$—$N(H)C(=O)O$—$(CH_2)_2$—O—$(CH_2)_3$—.

Formula C. Silicone-containing components of formulae A, B, B-1, B-2, B-3, B-4, B-5, B-6, B-7, B-8, B-9, B-10, B-11, B-12, B-13, B-14, B-15, B-18, and B-21 may include compounds of formula C, which are compounds of formula A, B, B-1, B-2, B-3, B-4, B-5, B-6, B-7, B-8, B-9, B-10, B-11, B-12, B-13, B-14, B-15, B-18, or B-21 having the structure:

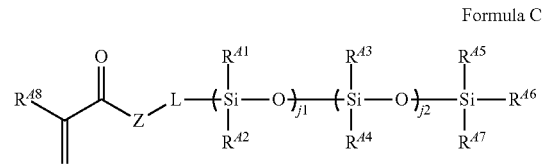

Formula C wherein
$R^{48}$ is hydrogen or methyl;
Z is O, S, or $N(R^{49})$; and
L, j1, j2, $R^{41}$, $R^{42}$, $R^{43}$, $R^{44}$, $R^{45}$, $R^{46}$, $R^{47}$, and $R^{49}$ are as defined in formula B or its various sub-formulae (e.g., B-1, B-2, etc.).

C-1. Compounds of formula C may include (meth)acrylates of formula C-1, which are compounds of formula C wherein Z is O.

C-2. Compounds of formula C may include (meth)acrylamides of formula C-2, which are compounds of formula C wherein Z is $N(R^{49})$, and $R^{49}$ is H.

C-3. Compounds of formulae C may include (meth)acrylamides of formula C-3, which are compounds of formula C wherein Z is $N(R^{49})$, and $R^{49}$ is $C_1$-$C_8$ alkyl that is unsubstituted or is optionally substituted as indicated above. Examples of $R^{49}$ include $CH_3$, —$CH_2CH(OH)CH_2(OH)$, —$(CH_2)_3$-siloxanyl, —$(CH_2)_3$—$SiR_3$, and —$CH_2CH(OH)CH_2$—O—$(CH_2)_3$—$SiR_3$ where each R in the foregoing groups is independently selected from trimethylsiloxy, $C_1$-$C_8$ alkyl (preferably $C_1$-$C_3$ alkyl, more preferably methyl), and $C_3$-$C_8$ cycloalkyl. Further examples of $R^{49}$ include: —$(CH_2)_3$—$Si(Me)(SiMe_3)_2$, and —$(CH_2)_3$—$Si(Me_2)$—[O—$SiMe_2]_{1-10}$—$CH_3$.

Formula D. Compounds of formula C may include compounds of formula D:

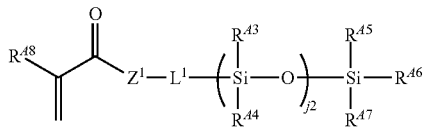

Formula D wherein $R^{48}$ is hydrogen or methyl;

$Z^1$ is O or $N(R^{49})$;

$L^1$ is alkylene containing 1 to 8 carbon atoms, or oxaalkylene containing 3 to 10 carbon atoms, wherein $L^1$ is optionally substituted with hydroxyl; and j2, $R^{43}$, $R^{44}$, $R^{45}$, $R^{46}$, $R^{47}$, and $R^{49}$ are as defined above in formula B or its various sub-formulae (e.g., B-1, B-2, etc.).

D-1. Compounds of formula D may include compounds of formula D-1, which are compounds of formula D wherein $L^1$ is $C_2$-$C_5$ alkylene optionally substituted with hydroxyl. Preferably $L^1$ is n-propylene optionally substituted with hydroxyl.

D-2. Compounds of formula D may include compounds of formula D-2, which are compounds of formula D wherein $L^1$ is oxaalkylene containing 4 to 8 carbon atoms optionally substituted with hydroxyl. Preferably $L^1$ is oxaalkylene containing five or six carbon atoms optionally substituted with hydroxyl. Examples include —$(CH_2)_2$—O—$(CH_2)_3$—, and —$CH_2CH(OH)CH_2$—O—$(CH_2)_3$—.

D-3. Compounds of formulae D, D-1, and D-2 may include compounds of formula D-3, which are compounds of formula D, D-1, or D-2 wherein $Z^1$ is O.

D-4. Compounds of formulae D, D-1, and D-2 may include compounds of formula D-4, which are compounds of formula D, D-1, or D-2 wherein $Z^1$ is $N(R^{49})$, and $R^{49}$ is H.

D-5. Compounds of formulae D, D-1, and D-2 may include compounds of formula D-5, which are compounds of formula D, D-1, or D-2 wherein $Z^1$ is $N(R^{49})$, and $R^{49}$ is $C_1$-$C_4$ alkyl optionally substituted with 1 or 2 substituents selected from hydroxyl, siloxy, and $C_1$-$C_6$ alkyl-siloxanyl-.

D-6. Compounds of formulae D, D-1, D-2, D-3, D-4, and D-5 may include compounds of formula D-6, which are compounds of formula D, D-1, D-2, D-3, D-4, or D-5 wherein j2 is 1.

D-7. Compounds of formulae D, D-1, D-2, D-3, D-4, and D-5 may include compounds of formula D-7, which are compounds of formula D, D-1, D-2, D-3, D-4, or D-5 wherein j2 is from 2 to 220, or from 2 to 100, or from 10 to 100, or from 24 to 100, or from 4 to 20, or from 4 to 10.

D-8. Compounds of formulae D, D-1, D-2, D-3, D-4, D-5, D-6, and D-7 may include compounds of formula D-8, which are compounds of formula D, D-1, D-2, D-3, D-4, D-5, D-6, or D-7 wherein $R^{43}$, $R^{44}$, $R^{45}$, $R^{46}$, and $R^{47}$ are independently $C1$-$C_6$ alkyl or siloxy. Preferably $R^{43}$, $R^{44}$, $R^{45}$, $R^{46}$, and $R^{47}$ are independently selected from methyl, ethyl, n-propyl, n-butyl, and trimethylsiloxy. More preferably, $R^{43}$, $R^{44}$, $R^{45}$, $R^{46}$, and $R^{47}$ are independently selected from methyl, n-butyl, and trimethylsiloxy.

D-9. Compounds of formulae D, D-1, D-2, D-3, D-4, D-5, D-6, and D-7 may include compounds of formula D-9, which are compounds of formula D, D-1, D-2, D-3, D-4, D-5, D-6, or D-7 wherein $R^{43}$ and $R^{44}$ are independently $C1$-$C_6$ alkyl (e.g., methyl or ethyl) or siloxy (e.g., trimethylsiloxy), and $R^{45}$, $R^{46}$, and $R^{47}$ are independently $C1$-$C_6$ alkyl (e.g., methyl, ethyl, n-propyl, or n-butyl).

Formula E. The silicone-containing component for use in the invention may comprise a multi-functional silicone-containing component. Thus, for example, the silicone-containing component of formula A may comprise a bifunctional material of formula E:

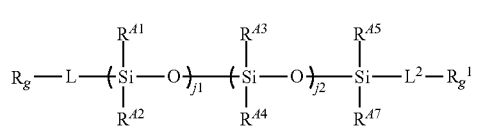

Formula E wherein

Rg, L, j1, j2, $R^{A1}$, $R^{A2}$, $R^{A3}$, $R^{A4}$, $R^{A5}$, and $R^{A7}$ are as defined above for formula B or its various sub-formulae (e.g., B-1, B-2, etc.);

$L^2$ is a linking group; and $Rg^1$ is a polymerizable group.

E-1. Compounds of formula E may include compounds of formula E-1, which are compounds of formula E wherein Rg and $Rg^1$ are each a vinyl carbonate of structure $CH_2$=CH—O—C(=O)—O— or structure $CH_2$=C($CH_3$)—O—C(=O)—O—.

E-2. Compounds of formula E may include compounds of formula E-2, which are compounds of formula E wherein Rg and $Rg^1$ are each (meth)acrylate.

E-3. Compounds of formula E may include compounds of formula E-3, which are compounds of formula E wherein Rg and $Rg^1$ are each (meth)acrylamide, wherein the nitrogen group may be substituted with $R^{49}$ (wherein $R^{49}$ is as defined above).

E-4. Suitable compounds of formulae E, E-1, E-2, and E-3 include compounds of formula E-4, which are compounds of formula E, E-1, E-2, or E-3 wherein j1 is zero and j2 is from 1 to 220, or j2 is from 1 to 100, or j2 is from 1 to 50, or j2 is from 1 to 20.

E-5. Suitable compounds of formulae E, E-1, E-2, and E-3 include compounds of formula E-5, which are compounds of formula E, E-1, E-2, or E-3, wherein j1 and j2 are independently from 4 to 100.

E-6. Suitable compounds of formulae E, E-1, E-2, E-3, E-4, and E-5 include compounds of formula E-6, which are compounds of formula E, E-1, E-2, E-3, E-4, or E-5 wherein $R^{A1}$, $R^{A2}$, $R^{A3}$, $R^{A4}$, and $R^{A5}$ are independently at each occurrence $C1$-$C_6$ alkyl, preferably they are independently $C_1$-$C_3$ alkyl, or preferably, each is methyl.

E-7. Suitable compounds of formulae E, E-1, E-2, E-3, E-4, E-5, and E-6 include compounds of formula E-7, which are compounds of formula E, E-1, E-2, E-3, E-4, E-5, or E-6 wherein $R^{A7}$ is alkoxy-alkyleneoxy-alkyl, preferably it is a methoxy capped polyethyleneoxyalkyl of formula $CH_3O$—$[CH_2CH_2O]_p$—$CH_2CH_2CH_2$, wherein p is a whole number from 1 to 50, or from 1 to 30, or from 1 to 10, or from 6 to 10.

E-8. Suitable compounds of formulae E, E-1, E-2, E-3, E-4, E-5, E-6, and E-7 include compounds of formula E-8, which are compounds of formula E, E-1, E-2, E-3, E-4, E-5, E-6, or E-7 wherein L comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

E-9. Suitable compounds of formulae E, E-1, E-2, E-3, E-4, E-5, E-6, E-7, and E-8 include compounds of formula E-9, which are compounds of formula E, E-1, E-2, E-3, E-4, E-5, E-6, E-7, or E-8 wherein $L^2$ comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

Examples of silicone-containing components suitable for use in the invention include, but are not limited to, compounds listed in Table 3. Where the compounds in Table 3 contain polysiloxane groups, the number of SiO repeat units in such compounds, unless otherwise indicated, is preferably from 3 to 100, more preferably from 3 to 40, or still more preferably from 3 to 20.

TABLE 3

1. mono-methacryloxypropyl terminated mono-n-butyl terminated polydimethylsiloxanes (mPDMS) (preferably containing from 3 to 15 SiO repeating units)
2. mono-acryloxypropyl terminated mono-n-butyl terminated polydimethylsiloxane
3. mono(meth)acryloxypropyl terminated mono-n-methyl terminated polydimethylsiloxane
4. mono(meth)acryloxypropyl terminated mono-n-butyl terminated polydiethylsiloxane
5. mono(meth)acryloxypropyl terminated mono-n-methyl terminated polydiethylsiloxane
6. mono(meth)acrylamidoalkylpolydialkylsiloxanes
7. mono(meth)acryloxyalkyl terminated mono-alkyl polydiarylsiloxanes
8. 3-methacryloxypropyltris(trimethylsiloxy)silane (TRIS)
9. 3-methacryloxypropylbis(trimethylsiloxy)methylsilane
10. 3-methacryloxypropylpentamethyl disiloxane
11. mono(meth)acrylamidoalkylpolydialkylsiloxanes
12. mono(meth)acrylamidoalkyl polydimethylsiloxanes
13. N-(2,3-dihydroxypropane)-N'-(propyl tetra(dimethylsiloxy) dimethylbutylsilane)acrylamide
14. N-[3-tris(trimethylsiloxy)silyl]-propyl acrylamide (TRIS-Am)
15. 2-hydroxy-3-[3-methyl-3,3-di(trimethylsiloxy)silylpropoxy]-propyl methacrylate (SiMAA)
16. 2-hydroxy-3-methacryloxypropyloxypropyl-tris(trimethylsiloxy)silane
17. mono-(2-hydroxy-3-methacryloxypropyl)-propyl ether terminated mono-n-butyl terminated polydimethylsiloxanes (OH-mPDMS) (containing from 4 to 30, or from 10 to 20, or from 4 to 8 SiO repeat units)

18.

$$\text{CH}_2=\text{C}(\text{CH}_3)-\text{C}(=\text{O})-\text{O}-(\text{CH}_2)_2-\text{O}-(\text{CH}_2)_3-[\text{Si}(\text{CH}_3)_2-\text{O}]_{j_2}-\text{Si}(\text{CH}_3)_2-(\text{CH}_2)_3\text{CH}_3$$

19.

$$\text{CH}_2=\text{CH}-\text{C}(=\text{O})-\text{NH}-(\text{CH}_2)_3-[\text{Si}(\text{CH}_3)_2-\text{O}]_{j_2}-\text{Si}(\text{CH}_3)_2-(\text{CH}_2)_3\text{CH}_3$$

20.

$$\text{CH}_2=\text{CH}-\text{C}(=\text{O})-\text{N}[(\text{CH}_2)_3-[\text{Si}-\text{O}]_{j_2}-\text{Si}-(\text{CH}_2)_3\text{CH}_3][(\text{CH}_2)_3-\text{Si}-[\text{O}-\text{Si}]_{j_2}-(\text{CH}_2)_3\text{CH}_3]$$

21.

$$\text{CH}_2=\text{CH}-\text{C}(=\text{O})-\text{N}[(\text{CH}_2)_3-[\text{Si}(\text{CH}_3)_2-\text{O}]_{j_2}-\text{Si}(\text{CH}_3)_2-(\text{CH}_2)_3\text{CH}_3][\text{CH}_2\text{CH}(\text{OH})\text{CH}_2\text{OH}]$$

22.

$$\text{CH}_2=\text{CH}-\text{C}(=\text{O})-\text{NH}-\text{CH}_2-\text{CH}(\text{OH})-\text{CH}_2-\text{O}-(\text{CH}_2)_3-[\text{Si}(\text{CH}_3)_2-\text{O}]_{j_2}-\text{Si}(\text{CH}_3)_2-(\text{CH}_2)_3\text{CH}_3$$

TABLE 3-continued

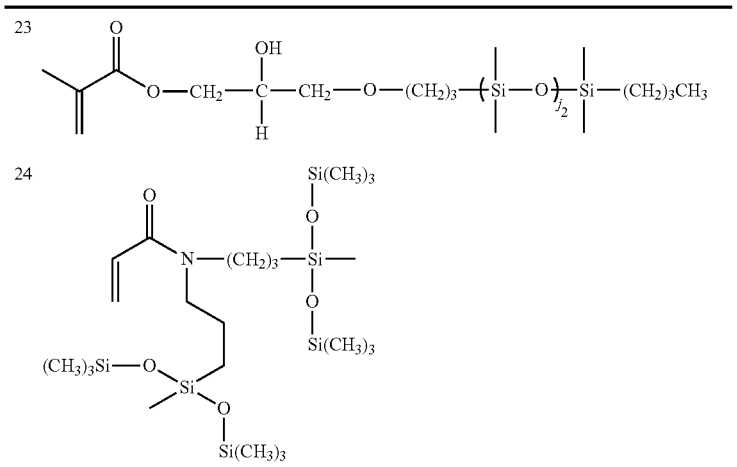

Additional non-limiting examples of suitable silicone-containing components are listed in Table 4. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE 4

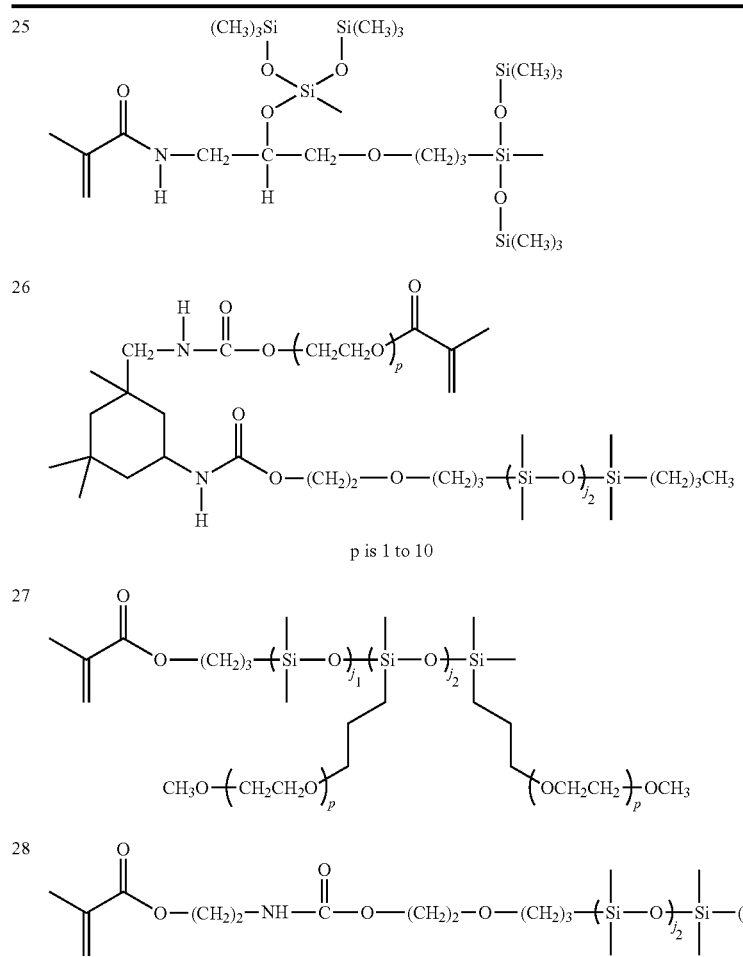

TABLE 4-continued
29 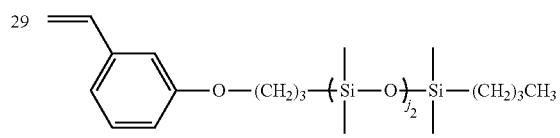
30  1,3-bis[4-(vinyloxycarbonyloxy)but-1-yl]tetramethyl-disiloxane
31  3-(vinyloxycarbonylthio) propyl-[tris (trimethylsiloxy)silane]
32  3-[tris(trimethylsiloxy)silyl] propyl allyl carbamate
33  3-[tris(trimethylsiloxy)silyl] propyl vinyl carbamate
34  tris(trimethylsiloxy)silylstyrene (Styryl-TRIS)
35 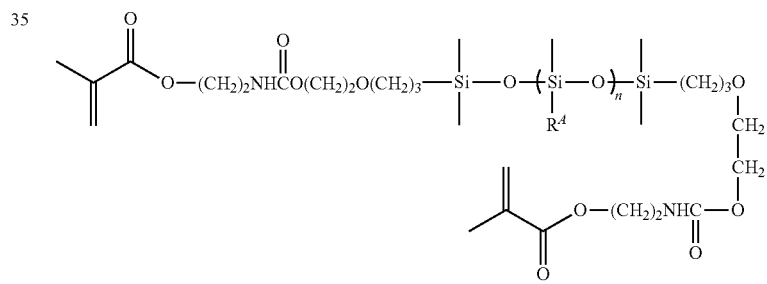
$R^A$ = $CH_3$ (a) or $CH_2CH_2CF_3$ (b) or $CH_2$—$(CH_2)_2$—$[OCH_2CH_2]_{1-10}$—$OCH_3$ (c); a + b + c = n
36 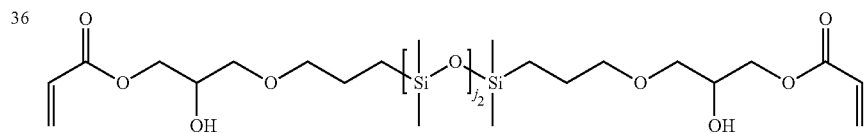
37 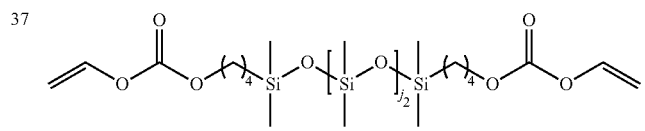
38 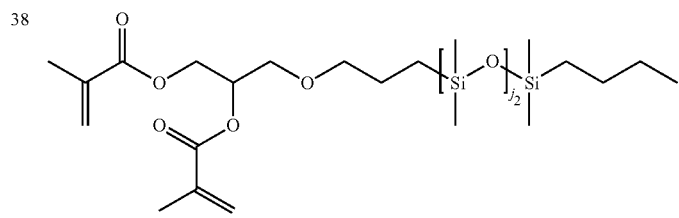
39 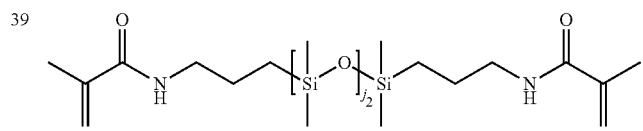
40 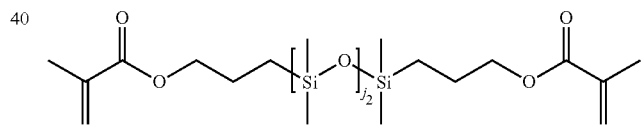

TABLE 4-continued

41

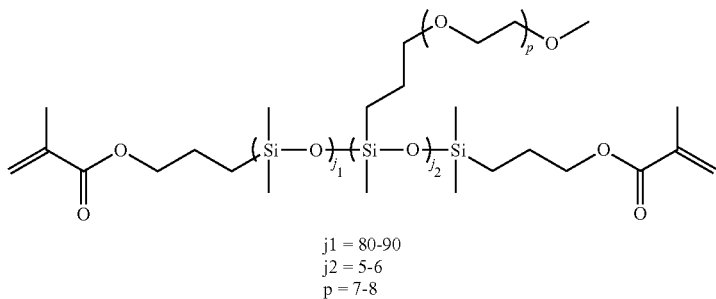

j1 = 80-90
j2 = 5-6
p = 7-8

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive monomer mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

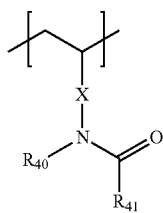

Formula G1

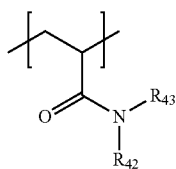

Formula G2 wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted C$_1$ to C$_2$ alkyl groups. X may be a direct bond, and R$_{40}$ and R$_{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methyl-propionamide, N-vinyl-N,N'-dimethylurea, N,N-dimethylacrylamide, methacrylamide, and acyclic amides of Formulae G2 and G3:

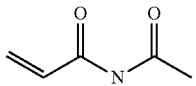

Formula G2

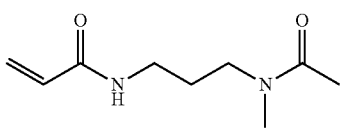

Formula G3

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

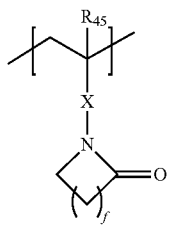

Formula G4 wherein $R_{45}$ is a hydrogen atom or methyl group; wherein f is a number from 1 to 10; wherein X is a direct bond, —(CO)—, or —(CONHR$_{46}$)—, wherein $R_{46}$ is a $C_1$ to $C_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth)acrylates. Any of the monomers listed as suitable hydrophilic monomers may be used as comonomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl) amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9CI) (PBT, phosphobetaine, CAS 163674-35-9, 2-methacryloyloxyethyl phosphorylcholine, 3-(dimethyl(4-vinylbenzyl)ammonio) propane-1-sulfonate (DMVBAPS), 3-((3-acrylamidopropyl) dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl) dimethylammonio)propane-1-sulfonate (APDAPS), 3-((3-(methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethylacetamide (PVMA), polydimethylacrylamide (PDMA), polyvinylacetamide (PNVA), poly hydroxyethyl(meth)acrylamide, polyacrylamide, and copolymers and mixtures thereof.

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multifunctional macromers, and prepolymers, to the reactive mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allyl methacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes α, ω-bismethacryloxypropyl polydimethylsiloxane.

Cross-linking agents that have rigid chemical structures and polymerizable groups that undergo free radical polymerization may also be used. Non-limiting examples of suitable rigid structures include cross-linking agents comprising phenyl and benzyl moieties, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described above, such as compounds of Formula E (and its sub-formulae) and the multi-functional compounds shown in Table 3.

Further Constituents

The reactive monomer mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445 the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbons. Specific diluents which may be used include 1-ethoxy-2-propanol, diisopropyl aminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus an α-diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine eoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N, N-dimethylamino)benzoate. Diazo thermal initiators may also be used, such as azobisisobutyronitrile (AIBN), 2,2'-azobis(2-methylbutyronitrile) (AMBN) or similar compounds.

Commercially available visible light initiator systems include Irgacure® 819, Irgacure® 1700, Irgacure® 1800, Irgacure® 819, Irgacure® 1850 (all from Ciba Specialty Chemicals) and Lucrin® TPO initiator (available from BASF). Commercially available UV photoinitiators include Darocur® 1173 and Darocur® 2959 (Ciba Specialty Chemicals). These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the ophthalmic devices of the invention may comprise, in addition to a hydroxyphenyl naphthotriazole of formula I, any of the polymerizable compounds and optional components described above.

Preferred reactive mixtures may comprise: a hydroxyphenyl naphthotriazole of formula I and a hydrophilic monomer.

Preferred reactive mixtures may comprise: a hydroxyphenyl naphthotriazole of formula I; and a hydrophilic monomer selected from DMA, NVP, HEMA, VMA, NVA, methacrylic acid, and mixtures thereof. Preferred are mixtures of HEMA and methacrylic acid.

Preferred reactive mixtures may comprise: a hydroxyphenyl naphthotriazole of formula I, a hydrophilic monomer, and a silicone-containing component.

Preferred reactive mixtures may comprise: a hydroxyphenyl naphthotriazole of formula I, a hydrophilic monomer, and a silicone-containing component comprising a compound of formula D (or its sub-formulae, such as D-1, D-2, etc.).

Preferred reactive mixtures may comprise: a hydroxyphenyl naphthotriazole of formula I, a hydrophilic monomer selected from DMA, NVP, HEMA, VMA, NVA, and mixtures thereof; a silicone-containing component comprising a compound of formula D (or its sub-formulae, such as D-1, D-2, etc.); and an internal wetting agent.

Preferred reactive mixtures may comprise: a hydroxyphenyl naphthotriazole of formula I, a hydrophilic monomer selected from DMA, HEMA and mixtures thereof; a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof; and a wetting agent (preferably PVP or PVMA). For the hydrophilic monomer, mixtures of DMA and HEMA are preferred. For the silicone containing component, mixtures of SiMAA and mPDMS are preferred.

The foregoing reactive mixtures may contain optional ingredients such as, but not limited to, one or more initiators, internal wetting agents, crosslinkers, other UV blockers, and diluents.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, hydrogels may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a silicone hydrogel contact lens may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble components such as inorganic salts or release agents, wetting agents, slip agents, pharmaceutical and nutraceutical compounds, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

Silicone hydrogel ophthalmic devices (e.g., contact lenses) according to the invention preferably include the following properties. All values are prefaced by "about," and the devices may have any combination of the listed properties. The properties may be determined by methods known to those skilled in the art, for instance as described in United States pre-grant publication US20180037690, which is incorporated herein by reference.

[H$_2$O] %: at least 20%, or at least 25%

Haze: 30% or less, or 10% or less

Kruss DCA) (°): 100° or less, or 50° or less

Tensile Modulus (psi): 120 or less, or 80 to 120

Dk (barrers): at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less

Some embodiments of the invention will now be described in detail in the following Examples.

UV-VIS Test Methods

Ultraviolet-visible spectra of organic compounds in solution were measured on a Perkin Elmer Lambda 45 or an Agilent Cary 6000i UV/VIS scanning spectrometer. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission or absorbance; and baseline correction was selected. For the Cary instrument, the scan range was 200-800 nm; the scan speed was 600 nm/min; the slit width was 2 nm; the mode was transmission or absorbance; and baseline correction was selected. A baseline correction was performed before samples were analyzed using the autozero function.

Ultraviolet-visible spectra of contact lenses were measured on a Perkin Elmer Lambda 45 UV/VIS or an Agilent Cary 6000i UV/VIS scanning spectrometer using packing solution. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission; and baseline correction was selected. Baseline correction was performed using cuvettes containing plastic two-piece lens holders and the same solvents. These two-piece contact lens holders were designed to hold the sample in the quartz cuvette in the location through which the incident light beam traverses. The reference cuvette also contained a two-piece holder. To ensure that the thickness of the samples is constant, all lenses were made using identical molds. The center thickness of the contact lens was measured using an electronic thickness gauge. Reported center thickness and percent transmission spectra are obtained by averaging three individual lens data.

It is important to ensure that the outside surfaces of the cuvette are completely clean and dry and that no air bubbles are present in the cuvette. Repeatability of the measurement is improved when the reference cuvette and its lens holder remain constant and when all samples use the same sample cuvette and its lens holder, making sure that both cuvettes are properly inserted into the instrument.

Ultraviolet-visible spectra of solid buttons are measured as described above except that no packing solution was used, the baseline correction was performed in air, and the percent transmission spectra are obtained from one button instead of averaging three individual button data.

EXAMPLES

The following abbreviations will be used throughout the Examples and Figures and have the following meanings:

BC: back or base curve plastic mold
FC: front curve plastic mold
Da: dalton or g/mole
kDa: kilodalton or an atomic mass unit equal to 1,000 daltons
mL: milliliter
L: liter
g: gram or grams
mg: milligram or milligrams
mmol: millimoles
eq: equivalent or equivalents
M: molar concentration
N: normal concentration
mM: millimolar concentration
cm: centimeter(s)
DMA: N,N-dimethylacrylamide (Jarchem)
HEMA: 2-hydroxyethyl methacrylate (Bimax)
PVP: poly(N-vinylpyrrolidone) (ISP Ashland)
TEGDMA: tetraethylene glycol dimethacrylate (Esstech)
AIBN: azobisisobutyronitrile
Irgacure 184: 1-hydroxy-cyclohexyl-phenyl ketone
Irgacure 819: bis(2,4,6-trimethylbenzoyl)-phenylphosphineoxide (BASF or Ciba Specialty Chemicals)
Irgacure 1870: blend of bis(2,6-dimethoxybenzoyl)-2,4,4-trimethyl-pentylphosphineoxide and 1-hydroxy-cyclohexyl-phenyl-ketone (BASF or Ciba Specialty Chemicals)
mPDMS: mono-n-butyl terminated monomethacryloxypropyl terminated polydimethylsiloxane ($M_n$=800-1000 daltons) (Gelest)
HO-mPDMS: mono-n-butyl terminated mono-(2-hydroxy-3-methacryloxypropyl)-propyl ether terminated polydimethylsiloxane ($M_n$=400-1000 daltons) (Ortec or DSM-Polymer Technology Group)
SiMAA: 2-propenoic acid, 2-methyl-2-hydroxy-3-[3-[1,3,3,3-tetramethyl-1-[(trimethylsilyl)oxy]disiloxanyl]propoxy]propyl ester (Toray) or 3-(3-(1,1,1,3,5,5,5-heptamethyltrisiloxan-3-yl)propoxy)-2-hydroxypropyl methacrylate
D3O: 3,7-dimethyl-3-octanol (Vigon)
DI water: deionized water
MeOH: methanol
IPA: isopropyl alcohol
TFA: trifluoroacetic acid
TSA: p-toluenesulfonic acid
E3NP: ethyl 3-nitropropionate
TEA: trimethylamine
tBuOH: tert-butanol
DPPA: diphenylphosphoryl azide
MHPP: methyl 3-(4-hydroxyphenyl)propanoate
EDC: ethyl dimethylaminopropyl carbodiimide hydrochloride
DIPCDI: diisopropyl carbodiimide
DMAP: N,N-dimethylaminopyridine
CH$_2$Cl$_2$: methylene chloride
B$_2$(pin)$_2$: bis(pinacolato)diboron
Norbloc: 2-(2'-hydroxy-5-methacrylyloxyethylphenyl)-2H-benzotriazole (Janssen)
PP: polypropylene which is the homopolymer of propylene
TT: Tuftec which is a hydrogenated styrene butadiene block copolymer (Asahi Kasei Chemicals)
Z: Zeonor which is a polycycloolefin thermoplastic polymer (Nippon Zeon Co Ltd)
TL03 lights: Phillips TLK 40W/03 bulbs
Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2 liter volumetric flask.

Example 1—Synthesis of Compound (E) as Shown in Scheme 1

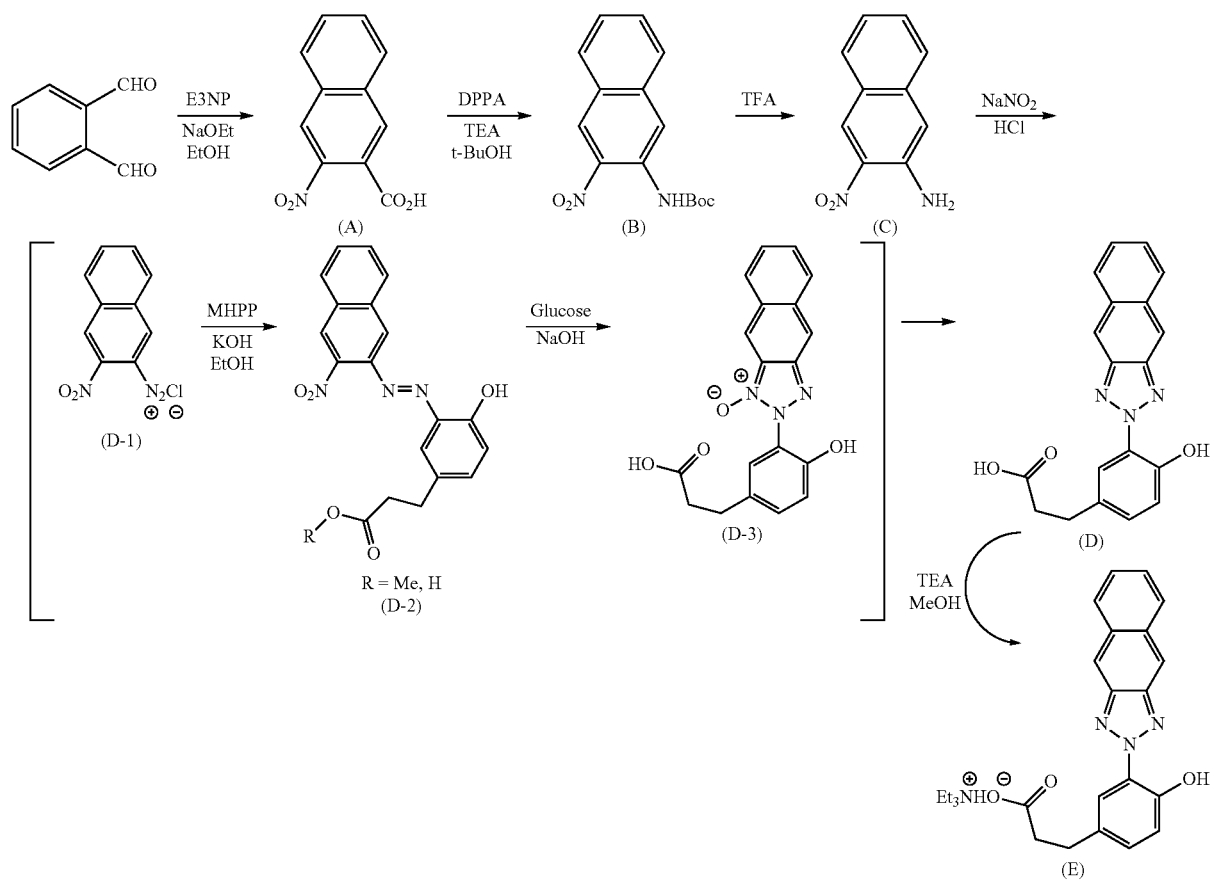

3-Nitro-2-naphthoic acid (A):

A solution of sodium ethoxide (111 mmol, 3 eq.) in 111 mL of absolute ethanol was added dropwise to a solution of ethyl 3-nitropropionate (6.0 g, 41 mmol, 1.1 eq.) in absolute ethanol (60 mL) at 0° C., resulting in an exotherm to 10° C. After stirring for 15 minutes, phthalaldehyde (5.0 g, 37 mmol, 1 eq.) in absolute ethanol (50 mL) was added dropwise to the reaction. The reaction was allowed to warm to room temperate and stirred for three days. Amberlite IR 120 H+ (80 g) was added, and the reaction stirred at room temperature overnight. The solution was diluted with ethyl acetate (600 mL) and gravity filtered. The filtrate was diluted with water (600 mL) and saturated brine (100 mL) and the layers were separated. The aqueous layer was extracted with additional ethyl acetate (300 mL). The combined organic layers were dried over sodium sulfate and concentrated under reduced pressure. The residue was dried under vacuum at 38° C. for 4 hours to give compound (A) (7.5 g, 93%) as an orange-brown solid which was used subsequently.

3-Nitronaphthalen-2-amine (C):

Compound (A) (7.5 g, 35 mmol) was dissolved in toluene (100 mL) and azeotroped with a Dean-Stark trap for 3 hours. After cooling to room temperature, triethylamine (9.6 mL, 69 mmol, 2 eq.) and tert-butanol (9.9 mL, 104 mmol, 3 eq.) were added, and the reaction was heated to 35° C. Diphenylphosphoryl azide (4.1 mL, 19 mmol, 0.55 eq.) was added causing the temperature to increase to 42° C. A second portion of diphenylphosphoryl azide (4.1 mL, 19 mmol, 0.55 eq.) was added, and the reaction was heated to 70° C., at which time the temperature quickly increased to 86° C. After refluxing for 2 hours, heating was stopped, and the reaction was allowed to stir at room temperature overnight. The reaction was diluted with dichloromethane (500 mL) and water (1 L). The layers were separated, and the aqueous layer was extracted with additional dichloromethane (300 mL). The combined organic layers were washed with saturated sodium bicarbonate (1 L) and concentrated under reduced pressure. The residue was purified over silica gel (260 g), eluting with a gradient of 0 to 70% ethyl acetate in heptanes to give compound (B) as a yellow oil.

Compound (B) was dissolved in dichloromethane (200 mL) and treated with trifluoroacetic acid (27 mL, 345 mmol, 10 eq.) and stirred at room temperature for 5 hours. Additional trifluoroacetic acid (40 mL, 519 mmol, 15 eq.) was added and the reaction stirred at room temperature overnight. The reaction was concentrated under reduced pressure. The residue was diluted with 10% sodium carbonate (300 mL) and stirred for 30 minutes. The mixture was extracted with ethyl acetate (2×250 mL). The combined organic layers were washed with saturated brine (100 mL) and concentrated under reduced pressure to give compound (C) (5.3 g, 82%) as a red orange solid.

3-(4-Hydroxy-3-(2H-naphtho[2,3-d][1,2,3]triazol-2-yl)phenyl)propanoic acid (D):

Due to the short reaction time, all reagents and solutions should be ready before experiment is started.

Preparation of a Coupler Solution:

Methyl 3-(4-hydroxyphenyl)propanoate (540 mg, 3 mmol) was dissolved in ethanol (12 mL) and the solution was cooled to −30° C. A solution of potassium hydroxide (950 mg, 16.9 mmol, 5.63 eq.) in water (3.85 g) was added two minutes before addition of the diazonium salt and the mixture was stirred in the cooling bath.

Preparation of Diazonium Salt Solution (D-1):

A suspension of compound (C) (565 mg, 3 mmol) in water (2.0 g) and 37% hydrochloric acid (1.47 g, 14.9 mmol, 4.97 eq.) was stirred at room temperature for 15 minutes. After cooling to 5° C., a solution of sodium nitrite (214 mg, 3.1 mmol, 1.03 eq.) in water (735 mg) was added over 1 minute. Water (500 mg) was used to rinse the vial. The reaction mixture was stirred in an ice/water bath for 3 minutes and was added to a cold solution of a coupler prepared in parallel. The reaction was stirred vigorously for 2 minutes. The cooling bath was removed, and reaction mixture was allowed to warm-up to room temperature over one hour. Analysis by liquid chromatography/mass spectrometry (LCMS) indicated formation of a mixture of intermediate methyl ester and carboxylic acid (D-2).

A solution of glucose (1.3 g, 7.2 mmol) in 2 N sodium hydroxide (12 mL, 24 mmol, 8 eq.) was added to the reaction mixture and stirred at ambient temperature. The formation of compound (D-3) was detected by LCMS after 1 hour. Subsequent reduction to compound (D) after 24 hours was also confirmed by LCMS. The reaction mixture was extracted with toluene (2×50 mL). The extracts were washed with 2 N sodium hydroxide (15 mL), and the toluene washes were discarded. The combined aqueous layer was acidified with acetic acid and extracted with ethyl acetate (2×100 mL) and concentrated under reduced pressure. Toluene (50 mL) was added and the solution again concentrated under reduced pressure to remove residual acetic acid.

The above procedure was repeated several times to yield a combined crude fraction of ~23 g, containing 5-7% of compound (D). Initial purification over silica gel (400 g) eluting with a gradient of 0 to 50% ethyl acetate in dichloromethane gave compound (D) (2 g, 70% purity). Final purification was accomplished on an AnaLogix Reverse Phase column (275 g) eluting with a gradient of 0 to 100% of tetrahydrofuran in water. The solid was triturated with methyl tert-butyl ether (20 mL) to give compound (D) (970 mg, 4.4% yield, 95% purity) as a yellow solid. $^1$H NMR (300 MHz, DMSO-$d_6$) δ 8.69 (s, 2H), 8.05 (dd, 2H), 7.86 (d, 1H), 7.41 (dd, 2H), 7.34 (dd, 1H), 7.13 (d, 1H), 2.86 (t, 2H), 2.57 (t, 2H).

Compound (D) possesses low solubility in commonly used solvents for UV spectroscopy. The absorption spectrum of the chromophore was obtained by converting compound (D) to its triethylammonium salt in methanol.

Triethylammonium 3-(4-Hydroxy-3-(2H-naphtho[2,3-d][1,2,3]triazol-2-yl)phenyl)-propanoate (E):

40 mg of compound (D) was stirred under ambient conditions in a solution of 100 mg of triethylamine in 5 mL of methanol. Once the mixture turned homogeneous, the volatiles were removed under reduce pressure. The residual solids were washed with ethyl acetate and vacuum filtered over a fritted glass funnel. The residual solid was washed with additional ethyl acetate prior to drying in a vacuum oven at 50° C.

The transmission spectra of 0.2 mM solutions of Norbloc® and compound (E) in methanol are shown in FIG. 1, showing that compound (E) was significantly more red shifted than Norbloc® and can thereby offer protection from high energy visible light. In addition, the significantly enhanced extinction coefficient of hydroxyphenyl naphthotriazoles, like compound (E), in comparison to the benzotriazole analog Norbloc®, was demonstrated with almost complete absorption to 400 nm even at the low concentration tested. Significant blocking of high energy visible radiation 400-450 nm was also obtained at very low concentration.

Example 2—Synthesis of Polymerizable Compound F as Shown in Scheme 2

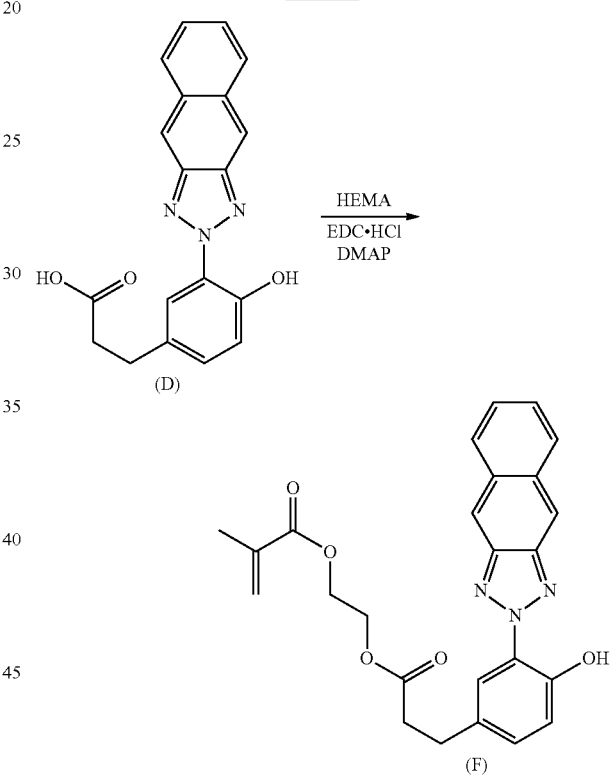

To prepare Compound (F), the following procedure may be followed. Compound (D), (200 mg, 0.60 mmol), 100 mg of N,N-dimethylamino pyridine (DMAP, catalytic), and 1.0 g of 2-hydroxyethyl methacrylate (HEMA) were heated in 50 mL of chloroform until the mixture became homogeneous. The solution was cooled to room temperature and 400 mg of 1-ethyl-3-(3-dimethylaminopropyl) carbodiimide hydrochloride (EDC.HCl, 2.08 mM) was added to the reaction mixture with constant stirring. Once all of compound (D) was consumed, the volatile components were evaporated under reduced pressure, and the resulting solids were washed with water over a fritted glass funnel. The resulting product was re-dissolved in dichloromethane and flushed through a silica gel plug. $^1$H NMR (CDCl$_3$) −δ 1.88 (m, 3H, CH3), 2.73 (t, 2H, CH$_2$), 3.02 (t, 2H, Ar—CH$_2$), 4.33 (s, 4H, CH$_2$O), 5.52 (m, 1H, vinylic), 6.06 (m, 1H, vinylic), 7.13 (d, 1H, Ar—H), 7.23 (dd, 1H, Ar—H), 7.37 (dd, 2H, Ar—H), 7.93 (dd, 2H, Ar—H), 8.37 (d, 2H, Ar—H), 8.47 (s, 2H, Ar—H), 11.55 (s, 1H, OH phenol). The ultraviolet-visible spectrum of compound (F) is shown in FIG. 2 in a 0.2 mM dichoromethane solution.

25 Grams (192 mmol) of HEMA was dissolved in 75 grams of ethylene glycol. Then, 2 grams (6 mmol) of TEGDMA was added to the solution and stirred until homogenous. The naphthotriazole monomer (F) (5.9 mg, 0.0132 mmole) was added to 45 mL of the above solution to provide a reactive monomer mixture containing 0.295 mM of compound (F). 20 Milligrams (0.12 mmol) of AIBN was added and stirred until the final solution was homogeneous. Small volumes of this reactive monomer mixture were transferred into vials, placed into a vacuum oven, degassed for one hour under vacuum at room temperature, and cured for 24 hours at 65° C. The polymeric buttons so formed were removed from the vials. The ultraviolet-visible spectrum of one button (Example 2 Button) was recorded and shown in FIG. 3. The thickness of the button was 0.52 cm.

Example 3—Synthesis of Polymerizable Compound I as Shown in Scheme 3

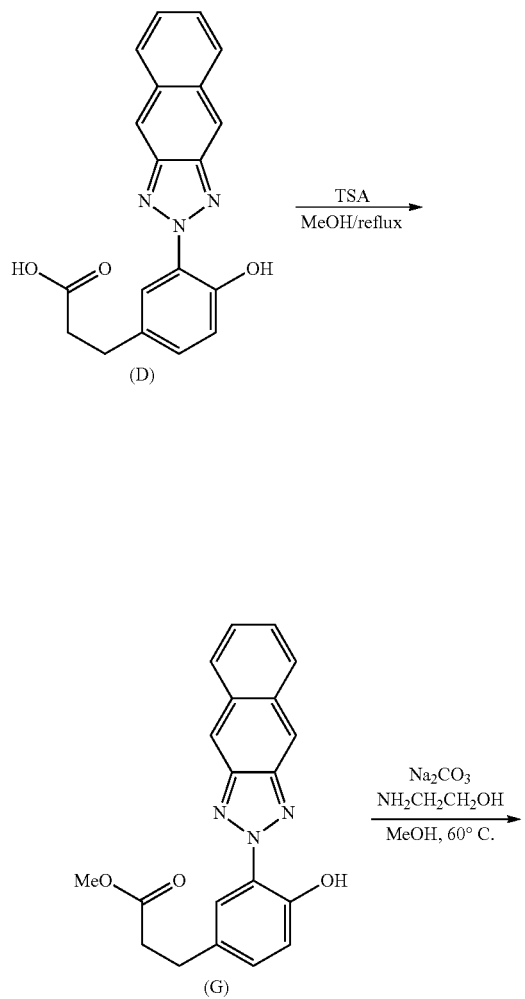

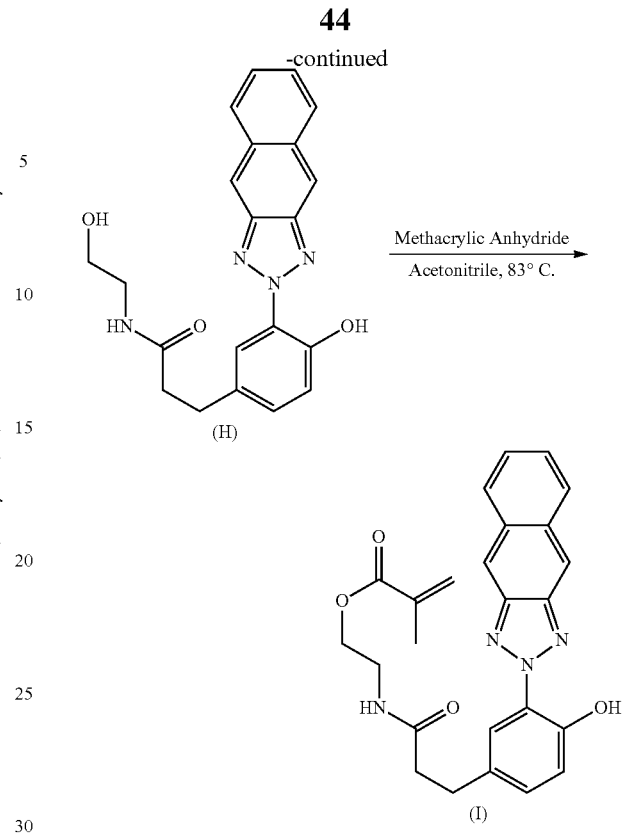

To prepare Compound (I), the following procedure may be followed. Compound (D) (1.0 g, 3.0 mmol) and p-toluenesulfonic acid (5 mg, catalyst) are dissolved in 100 mL MeOH and refluxed until the reaction is complete as determined by thin layer chromatography. The volatiles are evaporated under reduced pressure. The residue is dissolved in ethyl acetate or another suitable organic solvent and washed with aqueous sodium bicarbonate and then brine. The organic layer is separated, dried with Celite, and then evaporated under reduced pressure, yielding compound (G).

Compound (G) (427 mg, 1.23 mmol), 50 mg of anhydrous sodium carbonate (catalytic), and 500 mg of 2-aminoethanol (excess) are stirred in 10 mL of anhydrous methanol under a nitrogen atmosphere at 60° C. for 24 hrs. The mixture is cooled to room temperature, and poured into 50 mL of deionized water. The precipitate formed is filtered over a fritted glass funnel and washed two times with 50 mL of deionized water, after which it is dried in a rotary evaporator, followed by drying in a vacuum oven at 50° C., yielding compound (H).

A solution of the compound (H) (356 mg, 1.01 mmol) and 500 mg of methacrylic anhydride (3.25 mmol. 3.22 eq.) in 10 mL of anhydrous acetonitrile is heated at 83° C. in a round bottom flask equipped with a magnetic stirrer and reflux condenser. The reaction is monitored by thin layer chromatography and appeared complete after 24 hours, after which the mixture is cooled to room temperature and all volatiles evaporated under reduced pressure. The mixture is re-dissolved in ethyl acetate, extracted with aqueous sodium carbonate, concentrated under reduced pressure, and purified by chromatography over silica gel using ethyl acetate and dichloromethane. Evaporation of the solvents under reduced pressure yields compound (I).

Compound (I) may also be prepared via direct coupling of 2-ethanolamine with Compound (D), followed by acylation of the resulting amidoalcohol (H), as follows:

Compound (D) (1.0 g, 3.0 mmol) and 2-aminoethanol (3 g, ~50 mmol) are stirred in 50 mL of dichloromethane until homogeneous. 1-Ethyl-3-(3-dimethylaminopropyl)carbodiimide hydrochloride (EDC, 1.0 g, 5.2 mmol) is added to the solution which is continually stirred and monitored for the consumption of compound (D). Once the reaction is complete, the mixture is washed by dilute aqueous HCl to remove the excess amine and unreacted EDC. The organics are concentrated at reduced pressure and the product Compound (H) is purified by flash chromatography. Conversion of compound (H) to the methacrylate (I) may be achieved as described previously via reaction with an anhydride, or via carbodiimide promoted coupling of compound (H) and methacrylic acid.

Example 4—Silicone Hydrogel Formulations

Silicone hydrogels containing the hydroxyphenyl naphthotriazoles of the invention may be prepared according to the following procedure.

Master Batch: A 300 gram master batch of a reactive monomer mixture is prepared composed of 77 weight percent of the formulation listed in Table 5 and 23 weight percent of the diluent D3O. All of the components except the PVP are mixed in a jar under a nitrogen atmosphere at 29° C. for 90 minutes, after which the PVP is added and mixed for an additional 240 minutes at 30° C. Thereafter, the jar is capped and placed on a roller for 1050 minutes at room temperature. The reactive monomer mixture is then filtered through a 3 μm filter using a stainless steel syringe under pressure.

TABLE 5

| Component | Base Formulation (weight %) |
|---|---|
| mPDMS 1000 | 31.6 |
| SiMAA | 28.6 |
| DMA | 24.5 |
| HEMA | 6.13 |
| TEGDMA | 1.53 |
| PVP K90 | 7.14 |
| Irgacure 1870 | 0.35 |
| Irgacure 184 | 0.15 |
| Σ Components | 100 |

A desired amount of a hydroxyphenyl naphthotriazole compound is dissolved or dispersed in the Master Batch under a nitrogen atmosphere. The formulation is degassed at ambient temperature by applying vacuum (40 torr) for 45 minutes. Then, in a glove box with a nitrogen gas atmosphere and less than 0.1-0.2 percent oxygen gas, about 75-100 μL of the reactive mixture are dosed using an Eppendorf pipet at room temperature into the FC made of Zeonor. The BC made of 90:10 Z:TT is then placed onto the FC. The molds are equilibrated for a minimum of twelve hours in the glove box prior to dosing. Trays containing eight mold assemblies each are transferred into an adjacent glove box maintained at 65° C., and the lenses are cured from the top and the bottom for 20 minutes using 435 nm LED lights having an intensity of about 2 mW/cm² at the tray's location. The LED light sources are about 10 inches away from the trays.

The lenses are manually de-molded. The lenses are equilibrated in borate buffered packaging solution overnight and then stored in fresh borate buffered packaging solution thereafter. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels.

We claim:
1. An ophthalmic device comprising a free radical reaction product of (a) at least one compound of formula I:

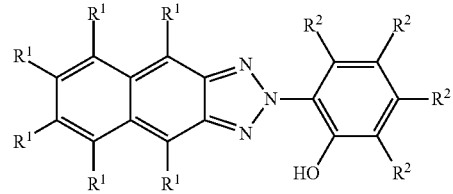

Formula I wherein:
$R^1$ at each occurrence is independently H, halo, $C_1$-$C_6$ alkyl, $C_3$-$C_{12}$ cycloalkyl, aryl, or aryl-$C_1$-$C_6$-alkyl;
at least one $R^2$ is a group of formula $R_g$-L, wherein $R_g$ is a polymerizable group and L is a linking group, and the remaining $R^2$ are independently at each occurrence H, $C_1$-$C_6$ alkyl, $C_3$-$C_{12}$ cycloalkyl, aryl, or aryl-$C_1$-$C_6$-alkyl, wherein L at each occurrence is independently $[CH_2]_m Y-[CH_2]_n-$, wherein m is a number from 1 to 6, n is a number from 1 to 6, Y is O, S, C(=O)O, $NR^3$, or C(=O)$NR^3$, and $R^3$ is H or $C_1$-$C_4$ alkyl; and
wherein each alkyl, cycloalkyl, and aryl group is unsubstituted or substituted; and
(b) at least one silicone-containing component and at least one hydrophilic monomer.

2. The ophthalmic device of claim 1 wherein $R^1$ is at each occurrence is independently H, chloro, $C_1$-$C_4$ alkyl, phenyl, or benzyl.

3. The ophthalmic device of any one of claims 1 to 2 wherein $R^2$ at each occurrence is independently H, $C_1$-$C_4$ alkyl, phenyl, benzyl, or Rg-L.

4. The ophthalmic device of claim 3 wherein Rg comprises styryl, vinyl carbonate, vinyl ether, vinyl carbamate, N-vinyl lactam, N-vinylamide, (meth)acrylate, or (meth) acrylamide.

5. The ophthalmic device of claim 4 wherein the linking group comprises $C_1$-$C_6$ oxaalkylene, $C_1$-$C_6$ thiaalkylene, $C_1$-$C_4$ alkylene-carboxylate-$C_1$-$C_4$ alkylene, $C_1$-$C_4$ alkylene-amide-$C_1$-$C_4$ alkylene, or $C_1$-$C_4$ alkylene-amine-$C_1$-$C_4$ alkylene.

6. The ophthalmic device of claim 4 further comprising at least one additional component selected from the group consisting of diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

7. The ophthalmic device of claim 6 wherein the at least one hydrophilic monomer is selected from the group consisting of hydrophilic (meth)acrylate, hydrophilic (meth) acrylamide monomers, ionic monomers, hydrophilic N-vinyl lactam and N-vinyl amide monomers, hydrophilic O-vinyl carbamates and O-vinyl carbonates monomers, hydrophilic vinyl compounds and mixtures thereof.

8. The ophthalmic device of claim 7 wherein the hydrophilic monomer is selected from the group consisting of acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth)acrylamide, N-(3-hydroxybutyl) (meth)acrylamide, N-(4-hydroxybutyl) (meth)acrylamide, 2-aminoethyl (meth)acrylate, 3-aminopropyl (meth)acrylate, 2-aminopropyl (meth)acrylate, N-2-aminoethyl (meth) acrylamides), N-3-aminopropyl (meth)acrylamide, N-2-aminopropyl (meth)acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile and mixtures thereof.

9. The ophthalmic device of claim 4 that is a contact lens, a corneal onlay, a corneal inlay, an intraocular lens, or an overlay lens.

10. The ophthalmic device of claim 6 wherein the at least one hydrophilic monomer is selected from the group consisting of N,N-dimethyl acrylamide, 2-hydroxyethyl methacrylate, N-vinyl pyrrolidone, N-vinyl-N-methylacetamide, N-vinyl acetamide, and mixtures thereof.

11. The ophthalmic device of claim 6 wherein the at least one silicone-containing component comprises (a) one or more polymerizable groups selected from the group consisting of (meth)acrylate,(meth)acrylamide, or mixtures thereof; (b) one or more optionally repeating siloxane units; and (c) one or more linking groups connecting the polymerizable groups to the siloxane units.

12. The ophthalmic device of claim 6 wherein the at least one silicone-containing component is at least one monofunctional polymerizable compound of formula B:

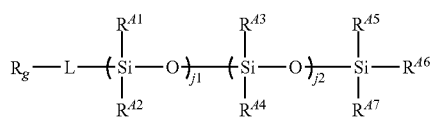

Formula B wherein: j1 is zero and j2 is from 1 to 20, and Rg is a polymerizable group;
L is a linking group;
$R^{A1}$, $R^{A2}$, $R^{A3}$, $R^{A4}$, $R^{A5}$, and $R^{A7}$ are independently at each occurrence $C_1$-$C_6$ alkyl, $C_3$-$C_{12}$ cycloalkyl, $C_1$-$C_6$ alkoxy, $C_4$-$C_{12}$ cyclic alkoxy, alkoxy-alkyleneoxy-alkyl, aryl, aryl-alkyl, haloalkyl, siloxy, fluoro, or combinations thereof, wherein each alkyl in the foregoing groups is optionally substituted with one or more hydroxy, amino, amido, oxa, carboxy, alkyl carboxy, carbonyl, alkoxy, carbamate, carbonate, halo, phenyl, or benzyl, each cycloalkyl is optionally substituted with one or more alkyl, hydroxy, amino, amido, oxa, carbonyl, alkoxy, carbamate, carbonate, halo, phenyl, or benzyl and each aryl is optionally substituted with one or more alkyl, hydroxy, amino, amido, oxa, carboxy, alkyl carboxy, carbonyl, alkoxy, carbamate, carbonate, halo, phenyl, or benzyl; and
$R^{A6}$ is siloxy, $C_1$-$C_8$ alkyl, or aryl, wherein alkyl and aryl may optionally be substituted with one or more fluorine atoms.

13. The ophthalmic device of claim 8 wherein the at least one silicone-containing component is selected from the group consisting of mono-methacryloxypropyl terminated mono-n-butyl terminated polydimethylsiloxanes (mPDMS) containing from 3 to 15 SiO repeating units; mono-acryloxypropyl terminated mono-n-butyl terminated polydimethylsiloxane containing from 3 to 20 SiO repeating units; mono-acryloxypropyl terminated mono-n-butyl terminated polydimethylsiloxane containing from 3 to 20 SiO repeating units; mono(meth)acryloxypropyl terminated mono-n-methyl terminated polydimethylsiloxane containing from 3 to 20 SiO repeating units; mono(meth)acryloxypropyl terminated mono-n-methyl terminated polydimethylsiloxane containing from 3 to 20 SiO repeating units; mono(meth)acryloxypropyl terminated mono-n-butyl terminated polydiethylsiloxane containing from 3 to 20 SiO repeating units; mono(meth)acryloxypropyl terminated mono-n-methyl terminated polydiethylsiloxane containing from 3 to 20 SiO repeating units; mono(meth)acryloxypropyl terminated mono-n-methyl terminated polydiethylsiloxane containing from 3 to 20 SiO repeating units; mono(meth)acrylamidoalkylpolydialkylsiloxanes containing from 3 to 20 SiO repeating units; mono(meth)acryloxyalkyl terminated mono-alkyl polydiarylsiloxanes containing from 3 to 20 SiO repeating units; 3-methacryloxypropyltris(trimethylsiloxy) silane (TRIS); 3-methacryloxypropylbis(trimethylsiloxy) methylsilane; 3-methacryloxypropylpentamethyl disiloxane mono(meth)acrylamidoalkylpolydialkylsiloxanes containing from 3 to 20 SiO repeating units; mono(meth)acrylamidoalkyl polydimethylsiloxanes containing from 3 to 20 SiO repeating units; N-(2,3-dihydroxypropane)-N'-(propyl tetra (dimethylsiloxy) dimethylbutylsilane)acrylamide; N-[3-tris (trimethylsiloxy)silyl]-propyl acrylamide; 2-hydroxy-3-[3-methyl-3,3-di(trimethylsiloxy)silylpropoxy]-propyl methacrylate (SiMAA); 2-hydroxy-3-methacryloxypropyloxypropyl-tris(trimethylsiloxy)silane; mono-(2-hydroxy-3-methacryloxypropyl)-propyl ether terminated mono-n-butyl terminated polydimethylsiloxanes (OH-mPDMS) containing from 4 to 30 SiO repeat units; and the silicone containing components of the following formulae where j2 is 3-20

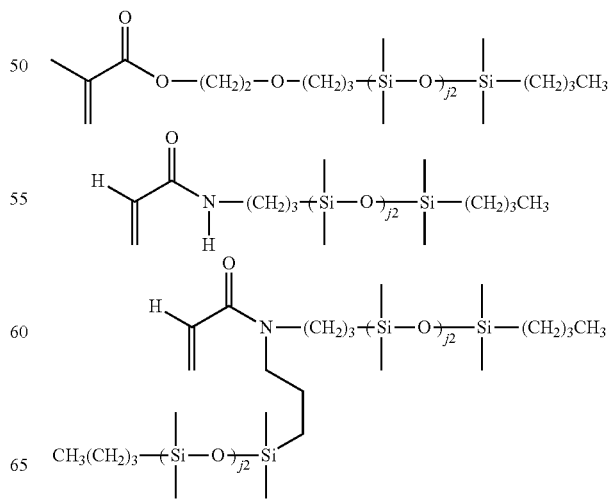

-continued

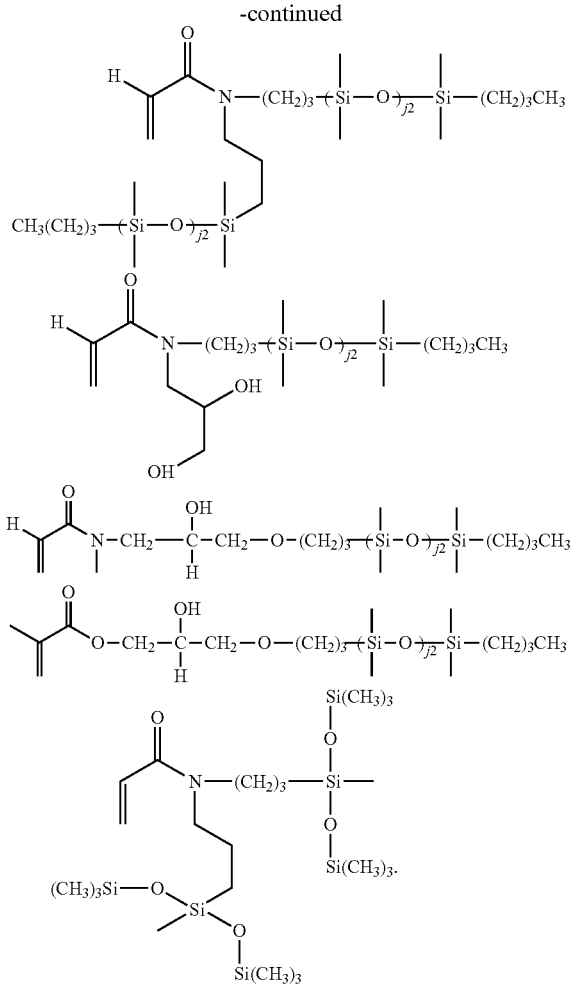

14. The ophthalmic device of claim 8 wherein the at least one silicone-containing component is selected from the group consisting of mono-methacryloxypropyl terminated mono-n-butyl terminated polydimethylsiloxane having 3-15 SiO repeating units, mono-(2-hydroxy-3-methacryloxypropyl)-propyl ether terminated mono-n-butyl terminated polydimethylsiloxane, 2-hydroxy-3-[3-methyl-3,3-di(trimethylsiloxy)silylpropoxy]-propyl methacrylate, and combinations thereof.

15. The ophthalmic device of claim 12 further comprising a polyamide.

16. The ophthalmic device of claim 15 wherein the polyamide is selected from the group consisting of polyvinylpyrrolidone, polyvinylmethylacetamide, polydimethylacrylamide, polyvinylacetamide, polyacrylamide, and copolymers and mixtures thereof.

17. The ophthalmic device of claim 8 further comprising a water content of at least about 20%, haze less than 30%, and oxygen permeability (Dk) of at least 80.

18. The ophthalmic device of claim 15 further comprising a water content of at least about 20%, haze less than 30%, and oxygen permeability (Dk) of at least 80.

19. The ophthalmic device of claim 18 further comprising a tensile modulus of 80 to 120 psi.

20. The ophthalmic device of claim 18 further comprising a water content of at least about 25%, haze less than 10%, and oxygen permeability (Dk) of at least 100.

* * * * *